United States Patent
Siejko et al.

(10) Patent No.: US 10,426,405 B2
(45) Date of Patent: Oct. 1, 2019

(54) METHODS AND DEVICES COMBINING MULTIPLE CARDIAC RATE MEASUREMENTS WITH ACTIVATION AND ARRHYTHMIA ANALYSIS CORRECTION

(71) Applicant: CARDIAC PACEMAKERS, INC., St. Paul, MN (US)

(72) Inventors: Krzysztof Z. Siejko, Maple Grove, MN (US); Amy Jean Brisben, St. Paul, MN (US); Stephen J. Hahn, Shoreview, MN (US); Keith L. Herrmann, Minneapolis, MN (US); Venugopal Allavatam, Fremont, CA (US)

(73) Assignee: CARDIAC PACEMAKERS, INC., St. Paul, MN (US)

( * ) Notice: Subject to any disclaimer, the term of this patent is extended or adjusted under 35 U.S.C. 154(b) by 67 days.

(21) Appl. No.: 15/362,859

(22) Filed: Nov. 29, 2016

(65) Prior Publication Data
US 2017/0156670 A1 Jun. 8, 2017

Related U.S. Application Data

(60) Provisional application No. 62/262,037, filed on Dec. 2, 2015.

(51) Int. Cl.
*A61B 5/00* (2006.01)
*A61B 5/021* (2006.01)
(Continued)

(52) U.S. Cl.
CPC .............. *A61B 5/686* (2013.01); *A61B 5/021* (2013.01); *A61B 5/0205* (2013.01); *A61B 5/0404* (2013.01); *A61B 5/04017* (2013.01); *A61B 5/0456* (2013.01); *A61B 5/1102* (2013.01); *A61B 5/14552* (2013.01); *A61B 5/4836* (2013.01); *A61B 5/7203* (2013.01); *A61B 5/7221* (2013.01); *A61B 5/0245* (2013.01); *A61B 5/02438* (2013.01); *A61B 5/0422* (2013.01); *A61B 5/04525* (2013.01); *A61B 5/1116* (2013.01); *A61B 5/1118* (2013.01); *A61B 7/04* (2013.01); *A61N 1/36585* (2013.01); *A61N 1/3702* (2013.01); *A61N 1/3987* (2013.01); *A61N 1/39622* (2017.08)

(58) Field of Classification Search
None
See application file for complete search history.

(56) References Cited

U.S. PATENT DOCUMENTS 6,721,597 B1 4/2004 Bardy et al.
6,754,528 B2 6/2004 Bardy et al.
(Continued)

*Primary Examiner* — Brian T Gedeon
(74) *Attorney, Agent, or Firm* — Seager, Tufte & Wickhem LLP

(57) ABSTRACT

In some examples, cardiac cycle detection may be used as a more or less default approach to cardiac activity tracking. Additional rate measurement relying on different sources or analyses may require extra power consumption over the cycle detection methods. Therefore, new methods and devices are disclosed that selectively activate a second cardiac rate measurement when needed. In some illustrative methods and devices, decisions are made as to whether and which previously collected data, if any, is to be discarded, replaced, or corrected upon activation of the second cardiac rate measurement.

20 Claims, 15 Drawing Sheets

(51) Int. Cl.

| | | |
|---|---|---|
| *A61B 5/04* | (2006.01) | |
| *A61B 5/0404* | (2006.01) | |
| *A61N 1/39* | (2006.01) | |
| *A61B 5/0452* | (2006.01) | |
| *A61B 5/11* | (2006.01) | |
| *A61B 5/1455* | (2006.01) | |
| *A61B 7/04* | (2006.01) | |
| *A61N 1/365* | (2006.01) | |
| *A61B 5/0205* | (2006.01) | |
| *A61B 5/042* | (2006.01) | |
| *A61B 5/0456* | (2006.01) | |
| *A61B 5/0245* | (2006.01) | |
| *A61B 5/024* | (2006.01) | |
| *A61N 1/37* | (2006.01) | |

(56) References Cited

U.S. PATENT DOCUMENTS

| | | |
|---|---|---|
| 7,248,921 B2 | 7/2007 | Palreddy et al. |
| 7,330,757 B2 | 2/2008 | Ostroff et al. |
| 8,116,867 B2 | 2/2012 | Ostroff |
| 8,160,686 B2 | 4/2012 | Allavatam et al. |
| 8,160,687 B2 | 4/2012 | Warren et al. |
| 8,160,697 B2 | 4/2012 | Warren et al. |
| 8,185,198 B2 * | 5/2012 | Palreddy ............ A61B 5/04525 607/5 |
| 8,409,107 B2 | 4/2013 | Sweeney et al. |
| 8,521,276 B2 | 8/2013 | Sweeney et al. |
| 8,565,878 B2 | 10/2013 | Allavatam et al. |
| 8,712,523 B2 | 4/2014 | Sanghera et al. |
| 8,831,711 B2 | 9/2014 | Freer et al. |
| 9,149,637 B2 | 10/2015 | Warren et al. |
| 9,451,892 B2 | 9/2016 | Siejko |
| 9,451,893 B2 | 9/2016 | Siejko et al. |
| 9,629,565 B2 | 4/2017 | Siejko |
| 2004/0230129 A1 * | 11/2004 | Haefner ......... A61B 17/320068 600/510 |
| 2009/0287103 A1 * | 11/2009 | Pillai .................. A61B 5/0245 600/509 |
| 2015/0196758 A1 | 7/2015 | Stahmann et al. |
| 2017/0112399 A1 | 4/2017 | Brisben et al. |
| 2017/0113040 A1 | 4/2017 | Brisben et al. |
| 2017/0113050 A1 | 4/2017 | Brisben et al. |
| 2017/0113053 A1 | 4/2017 | Brisben et al. |
| 2017/0156617 A1 | 6/2017 | Allavatam et al. |

* cited by examiner

METHODS AND DEVICES COMBINING MULTIPLE CARDIAC RATE MEASUREMENTS WITH ACTIVATION AND ARRHYTHMIA ANALYSIS CORRECTION

CROSS REFERENCE TO RELATED APPLICATIONS

The present application claims the benefit of and priority to U.S. Provisional Patent Application Ser. No. 62/262,037, titled METHODS AND DEVICES COMBINING MULTIPLE CARDIAC RATE MEASUREMENTS WITH ACTIVATION AND ARRHYTHMIA ANALYSIS CORRECTION, filed Dec. 2, 2015, the disclosure of which is incorporated herein by reference.

BACKGROUND

Many existing implantable or wearable cardiac rhythm management products, such as monitoring devices, pacing devices, and/or defibrillators, rely on the detection of individual cardiac cycles or "beats" in an electrical cardiac signal, such as the cardiac electrogram, surface electrocardiogram (ECG), and/or the subcutaneous ECG, to obtain a measurement of the rate of cardiac activity. Cardiac cycle detection is not the only available manner of obtaining a cardiac rate from the electrical cardiac signal, and other data sources may also provide cardiac rate measures.

For devices having plural cardiac rates available for use, new and alternative approaches to managing rate measurements from plural methodologies are desired.

OVERVIEW

The present inventors have recognized, among other things, that continuous improvement is allowing devices to move beyond merely using cardiac cycle detection to track cardiac activity. New and different methods of integrating additional cardiac activity sources are desired.

In some examples, cardiac cycle detection may be used as a default approach to cardiac activity tracking. Additional rate measurement relying on different sources or analysis may require extra power consumption over the cycle detection methods. Therefore, new methods and devices are disclosed that selectively activate a second cardiac rate measurement when needed. In some illustrative methods and devices, decisions are made as to whether and which previously collected data, if any, is to be discarded, replaced, or corrected upon activation of the second cardiac rate measurement.

This overview is intended to briefly introduce the subject matter of the present patent application, and is not intended to provide an exclusive or exhaustive explanation of the invention. The detailed description is included to provide further information.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
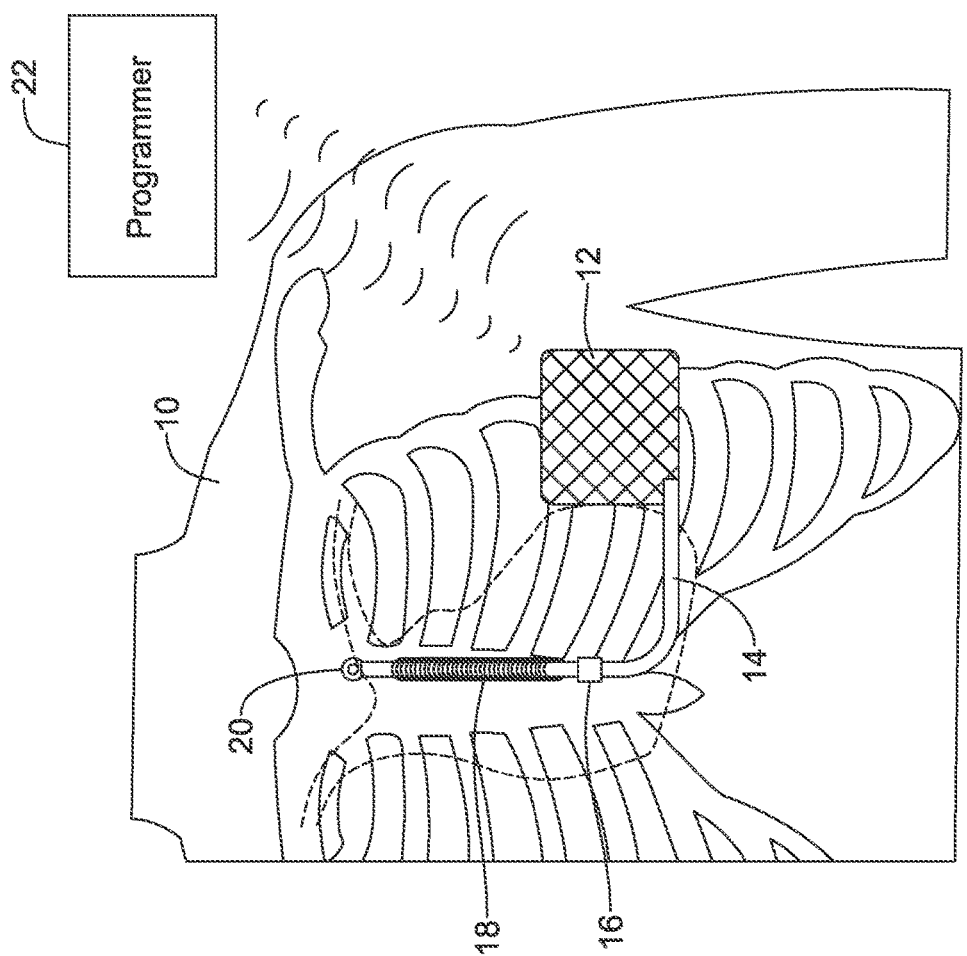
FIG. 1 shows an illustrative implantable cardiac rhythm management system.

FIG. 1 shows the S-ICD System™ from Cameron Health, Inc., and Boston Scientific Corporation, as implanted in a patient. The system is implanted in a patient 10 with a canister 12 in the left axilla at about the level of the cardiac apex. A lead 14 is placed subcutaneously, beneath the skin and over the ribcage of the patient, with a first portion extending along the inframammary crease to the xiphoid, and then superiorly parallel to and about 1-2 cm to the left of the sternum. A proximal sense electrode 16, shocking coil electrode 18, and distal tip sense electrode 20 are provided along the parasternal portion of the lead 14. The entire system is implanted outside of the ribcage.

The canister 12 may include componentry appropriate for communication (such as RF communication, inductive telemetry or other suitable communication linkage) with an external device such as a programmer 22. For example, during an implantation procedure, once the canister 12 and lead 14 are placed, the programmer 22 may be used to activate the canister 12 and/or direct/observe diagnostic or operational tests. After implantation, the programmer 22 may be used to non-invasively determine the status and history of the implanted device. The programmer 22 in combination with the canister 12 may also allow annunciation of statistics, errors, history and potential problems to the user/medical practitioner, and may also allow for updating of programming in the canister 12.

In some examples, the present invention may be implemented in a system as shown in FIG. 1. In other examples, an implantable or wearable cardiac monitor may have multiple electrodes on a housing and/or lead to define two or more sensing vectors. Leadless devices, such as leadless cardiac pacemakers for implantation inside the heart, may have multiple sensing electrodes on or extending from a canister or housing to define multiple sensing vectors. Wearable defibrillators or pacemakers may also provide multiple cutaneous electrodes on the anterior and/or posterior thorax of the patient, and may even include indifferent electrodes elsewhere such as on a limb. Transvenous and/or epicardial implantable devices may have an active housing adapted for use in sensing along with plural electrodes for sensing on one or more leads, as is well known in the art. For example, a transvenous device may have a right ventricular lead with atrial and ventricular sensing electrodes as well as an indifferent electrode on the canister.

Specific to the device shown in FIG. 1, unlike prior art defibrillators and pacemakers that include electrodes in or on the heart, the device uses only far-field electrodes outside the ribcage and away from the heart for detecting cardiac activity. This can make counting cardiac cycles more difficult, as the source of the detected signal may be harder to distinguish. For example, while a ventricular depolarization detected with a transvenous, intracardiac electrode may be quite sharp and narrow in width, the same signal will be wider and less sharp when detected in the far field. In some field products, T-wave overdetection has been observed in which individual cardiac cycles are counted twice, with a detection occurring on the R-wave and again on the T-wave. While significant effort is expended to avoid and/or identify and correct such overdetection, further improvements are desirable.

Figure 4:
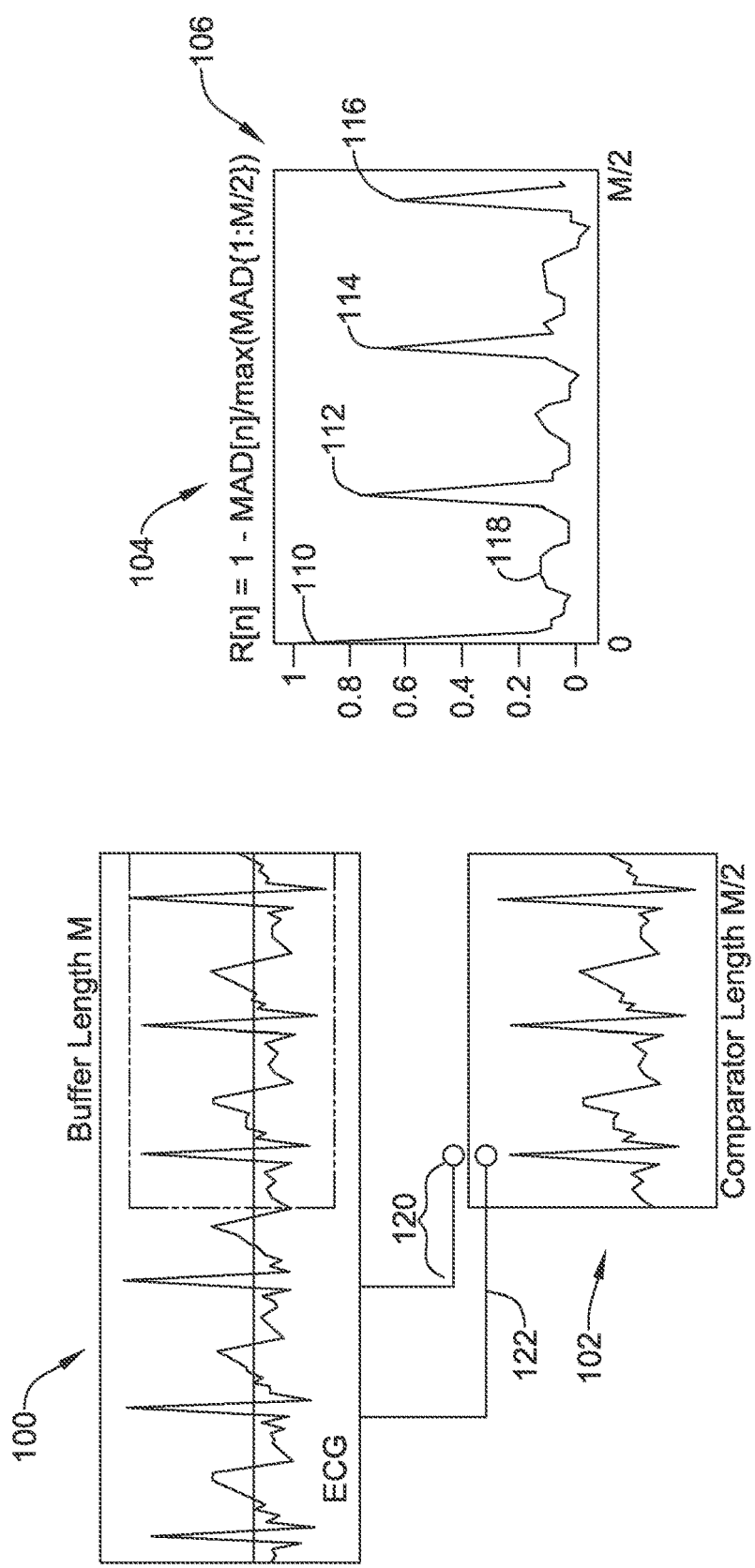
FIG. 4 shows an illustrative method of cardiac rate calculation using blocks of data, rather than detected cardiac cycles.

One approach is to use a rate relying on detecting cardiac cycles as well as a second cardiac rate measure obtained by another approach. The second cardiac rate may be obtained in various ways. Some examples may use cardiac rate measurements illustrated in copending U.S. patent application Ser. No. 14/819,817, Ser. No. 14/819,851, and Ser. No. 14/819,889, the disclosures of which are incorporated herein by reference (FIG. 4, below, shows a high level example). Other examples may use spectral content to determine a cardiac rate, or may reference data other devices. For example, a device as in FIG. 1 may communicate to a second implantable device, such as a monitor or leadless cardiac pacemaker implanted inside the heart, to obtain a rate therefrom. See, for example, US PG Patent Application Publication 20150196758, titled SYSTEMS AND METHODS FOR DETECTING CARDIAC ARRHYTHMIAS, the disclosure of which is incorporated herein by reference. Other examples may rely on a different data type, such as blood pressure data, pulse oximetry, cardiac motion, or heart sounds, for example, to determine or estimate cardiac rate.

Some examples focus on determining whether and when to activate a second rate calculation. Some further examples focus on determining which data to use and/or correct from the first rate calculation when the second rate calculation is operating. In any of the following examples, when a correction is made to data, an associated report may be generated or a marker placed in a stream of data to facilitate later physician review. For example, physicians often review stored episodes of cardiac data relating to occasions when therapy has been delivered, or a device has prepared to deliver therapy even if therapy is ultimately withheld. Reports showing data associated with therapy delivery or preparations may include specific markers indicating correction of data, whether for addressing overdetection by a cardiac cycle detection system, or for correcting or changing data related to whether a device has identified an arrhythmia in an X/Y counter or other analytic tool. Thus the results of analysis using a second cardiac rate that are at variance with results using a first cardiac rate or detection scheme can be presented to the physician for greater clarity and understanding.

Figure 2:
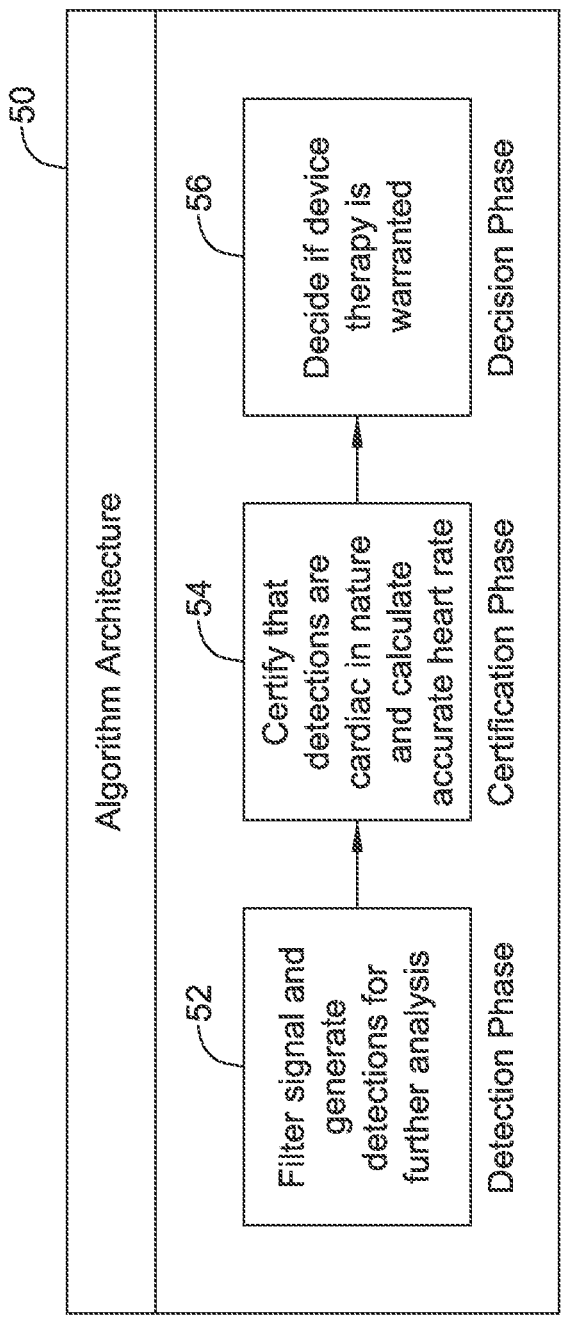
FIG. 2 shows an illustrative cardiac signal analysis architecture.

FIG. 2 shows an illustrative cardiac signal analysis architecture. The architecture 50 includes a detection phase 52 in which the input signal is filtered and cardiac cycle detections are generated for further analysis. Filtering may include both analog domain and digital domain filtering. For example a bandpass filter may be applied in the analog domain to remove DC and high frequency content, for example, using ranges of 3 to 40 Hz. Additional band stop filtering may be applied in the digital domain to remove 50/60 Hz line noise, and additional band-pass filtering may be performed to obtain desired cardiac signal bands in the range of between about 3-10 Hz and about 30-40 Hz. Other filter architectures may be used. Some examples related to filtering may be found in U.S. Provisional Patent Application 62/262,043, titled AUTOMATIC DETERMINATION AND SELECTION OF FILTERING IN A CARDIAC RHYTHM MANAGEMENT DEVICE, the disclosure of which is incorporated herein by reference.

Figure 3:
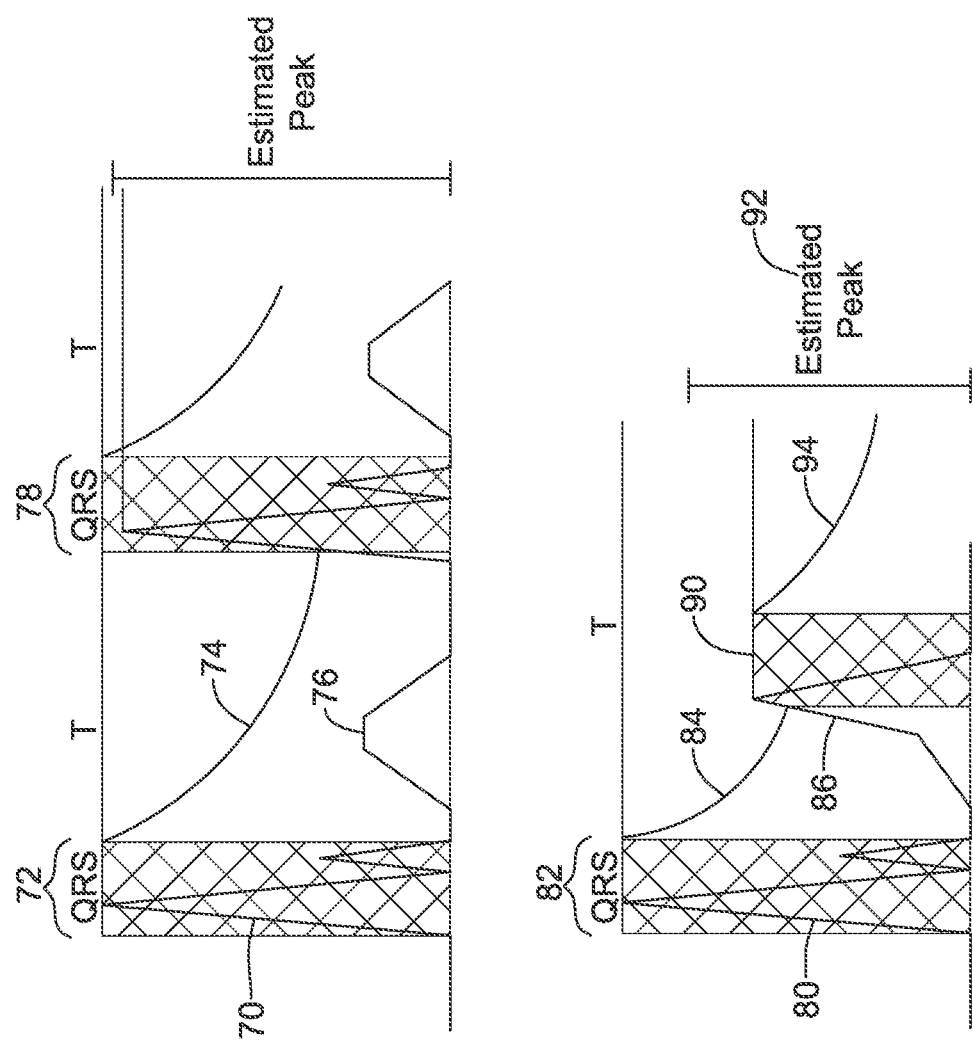
FIG. 3 shows operation of a detection profile to detect cardiac cycles using the R-wave, and shows an illustrative difficulty referred to as T-wave overdetection.

FIG. 3 shows an example of cycle detection. Some examples of cardiac cycle detection may be found, for example, in U.S. Pat. No. 8,565,878, titled ACCURATE CARDIAC EVENT DETECTION IN AN IMPLANTABLE CARDIAC STIMULUS DEVICE, the disclosure of which is incorporated herein by reference.

Detections generated by detection phase 52 pass to certification phase 54. Certification phase 54 may be designed to remove or correct for detections that are non-cardiac in nature, passing only those that are cardiac and not double detected for use in rate calculation. Certification may include, for example, identification and removal of cycle detections caused by noise, saturation, or wandering baseline as discussed, among other examples, in U.S. Pat. No. 7,248,921, titled METHODS AND DEVICES FOR PERFORMING CARDIAC WAVEFORM APPRAISAL, U.S. Pat. No. 8,712,523, titled IMPLANTABLE DEFIBRILLATOR SYSTEMS AND METHODS WITH MITIGATIONS FOR SATURATION AVOIDANCE AND ACCOMMODATION, and U.S. Pat. No. 8,831,711, titled IMPLANTABLE CARDIAC SYSTEMS WITH BASELINE CORRECTION IN RESPONSE TO NOISE DETECTION, the disclosures of which are incorporated herein by reference.

Certification phase 54 may also remove overdetections using, for example, methods and devices shown in U.S. Pat. Nos. 8,160,686 and/or 8,160,687, both titled METHODS AND DEVICES FOR ACCURATELY CLASSIFYING CARDIAC ACTIVITY, the disclosures of which are incorporated herein by reference. Certification phase 54 may also use methods (for transvenous systems in particular) to identify and eliminate far-field detection where only near field detection is desired. Certification phase 54 may be omitted in some examples.

Cardiac rate may be calculated using by measuring the intervals between individual detections that have been certified as cardiac and correct. A set of 1 to 8 intervals may be averaged to obtain an average cycle length, which can then be mathematically converted to a rate. For example, a 4 RR average may be the average of the previous four intervals between certified R-wave detections, and may be used to determine cardiac rate, where a 4 RR average of 500 milliseconds would equal to 120 beats per minute (BPM).

Decision phase 56 operates to decide whether device therapy is warranted, for those devices that can deliver therapy. Decision phase 56 may rely on detected cardiac rate along, or a combination of cardiac rate and other factors such as factors related to cardiac signal shape using, for example, R-waves, QRS complex, or other parts of the cardiac electrical signal, or non-cardiac electrical signals such as heart sounds, blood pressure measurements, patient activity or posture, etc. Some examples of decision phase may have a tiered approach in which, if the cardiac rate is below a tachycardia threshold, therapy is withheld, while if cardiac rate is above a ventricular fibrillation threshold, therapy delivery is considered necessary, while rates between the tachycardia threshold and ventricular fibrillation threshold warrant further analysis using, for example, static or dynamic template matching, width, or other factors.

A common approach, referenced below in several places, is for the decision phase to itself have two parts. A first decision is made as to whether a particular iteration of the architecture's operation indicates a treatable condition. This decision is tied to each cardiac cycle detection, or to only those detections that pass certification phase 54. A set of first decisions is retained in a counting filter, for example, an X/Y filter or a number-of-intervals-to-detect (NID) filter. As used herein, the phase "X/Y filter" should be understood to include both NID and X/Y filter approaches.

An X/Y filter, for example, tracks how many iterations of the decision phase 56 come to the conclusion that a treatable condition may exists (X) of a preceding set of iterations (Y). Typical thresholds for X/Y may be 8/12, 18/24, 30/40, for example. Various analysis and manipulations may be used for an X/Y filter. For example, in an analysis using a 4 RR average, explained above, once the 4 RR average exceeds a fast rate threshold, the X/Y filter may go from 0/Y to 1/Y, in a conservative method. Alternatively, for a 4 RR average, the first time the rate goes above the fast rate threshold, the X/Y filter may jump to 4/Y, in an aggressive method, where the use of the larger seeding is based on the knowledge that it took several fast cardiac cycle detections to get the 4 RR average over the threshold. Other manipulations may, for example, reduce the X/Y filter by steps of 1 to 3 if a cardiac cycle detection from the detection phase 52 fails at certification 54 due to noise and/or overdetection analysis. As the X/Y filter operates, new analysis outcomes go into and out of the filter data in a first in-first out manner.

The second stage or tier of analysis in the decision phase 56 may look at the overall rhythm using the X/Y filter output. For example, a threshold for treatable condition declaration may take place at an X/Y filter level of 18/24. Some examples may further apply rules for persistence, for example as described in U.S. Pat. No. 8,160,697, titled METHOD FOR ADAPTING CHARGE INITIATION FOR AN IMPLANTABLE CARDIOVERTER-DEFIBRILLATOR, the disclosure of which is incorporated herein by reference, to require that the treatable overall rhythm remain in place for one or several consecutive cycle detections.

Other examples for decision phase 56 methods/devices may be bound in U.S. Pat. No. 7,330,757, titled METHOD FOR DISCRIMINATING BETWEEN VENTRICULAR AND SUPRAVENTRICULAR ARRHYTHMIAS, in which both rate and morphology analysis may be used in a tiered fashion. For example, a ventricular tachycardia (VT) rate zone may be defined as well as a ventricular fibrillation (VF) rate zone, with the boundary for VF at a higher rate than VT. When the calculated rate is in the VT zone, morphology analysis, such as the matching of detected cardiac cycles to a template, or to each other, or assessment of the individual cycles using a metric such as width, is applied. In an example, VT zone cycles having poor template correlation relative to a normal sinus rhythm (NSR) template, and which are wide or are inconsistent in shape, may be deemed treatable; those which match the NSR and/or which are narrow and match one another may be deemed non-treatable. Continuing the example, when the rate is found to be in the VF zone, each detected cycle associated with such a rate would be found treatable.

Additional analysis may be performed using methods shown in U.S. Pat. No. 9,149,637, titled ADAPTIVE CONFIRMATION OF TREATABLE ARRHYTHMIA IN IMPLANTABLE CARDIAC STIMULUS DEVICES, the disclosures of which are incorporated herein by reference. These methods may manipulate the thresholds used in the decision phase upon completion of preparation for therapy delivery such as, for example, in a defibrillator system where several seconds may pass while a therapy delivery energy is generated by charging one or several capacitors to desired voltage/energy level.

If all the applicable rules are met, then therapy delivery will be deemed appropriate. Therapy delivery may include anti-tachycardia pacing, defibrillation or cardioversion therapy, a command to a separate device to deliver therapy, or delivery of a therapeutic substance, in various examples. For high power therapy such as defibrillation, there may be a need to continue operating the architecture 50 while therapy preparations are made, such as charging a high-power capacitor; the noted U.S. Pat. Nos. 8,160,697 and 9,149,637 describe certain illustrative methods. For non-therapy devices, such as monitoring systems, the outcomes at decision phase 56 may be used to activate data recording or storage for later retrieval, or to activate a patient alarm or alert, or to telemeter data related to unusual or elevated rate conditions to a second device/system.

FIG. 3 shows use of a detection profile to detect cardiac cycles using the R-wave as a detection target. The example also shows T-wave overdetection. A cardiac electrical signal is shown at 70; the example is based on a subcutaneous electrocardiogram, though signal 70 could as well be a cutaneously captured signal instead.

A first cardiac cycle detection is shown at 72, corresponding to the QRS complex of a patient's cardiac cycle. The shaded region is a "refractory" period in which no further detected cycles are declared to allow the QRS complex to finish prior to enabling new detections to occur. A time decaying detection threshold is depicted at 74, and starts at a level defined by prior detected cycle amplitude(s). The threshold 74 decays over time until the cardiac signal 70 crosses the detection threshold 74, generating another cardiac cycle detection at 78, again a QRS complex. The overall shape of the threshold 74 may be defined according to a "detection profile", as further detailed throughout U.S. Pat. No. 8,565,878, for example. Signal 70 has a relatively small T-wave 76, at least in proportion to the QRS complex height 72, 78, making accurate detection of cardiac cycles relatively simple.

A second signal is shown at 80. Here, again, a QRS complex is detected at 82 with corresponding refractory period, followed by the application of the detection threshold at 84. This time, however, the T-wave at 86 is larger relative to the QRS complex 82, causing a second cycle detection to occur at 90. The result is malsensing of the signal 80, with two cardiac cycle detections at 82, 90 for a single cardiac cycle having the P-Q-R-S-T waves therein. Malsensing of this sort can be perpetuated by the calculation of the estimated peak 92 of the cardiac cycle detections 82, 90. For example, the estimated peak 92 would typically be used to control the overall height of the detection thresholds 74, 84, using parameters provided by the detection profile. Further discussion of this type of T-wave overdetection is provided in U.S. Pat. No. 8,565,878, including some mitigations.

Even with various mitigations in place, overdetection of cardiac cycles based on oversensing of the cardiac signal (or non-cardiac signals) occurs in implantable and wearable therapy systems, causing unnecessary and inappropriate charging and/or therapy delivery. In monitoring systems, overdetection/oversensing can create unnecessary alerts and may fill data recorders with unhelpful data demonstrating malsensing rather than sought after intermittent cardiac impairments. For these and other reasons, additional efforts have been made to identify cardiac rate by other analyses.

FIG. 4 shows an illustrative method of cardiac rate calculation using blocks of data, rather than detected cardiac cycles. The drawing and following discussion provides a high level overview of several methods that may be used for generating a second cardiac rate estimate; additional details may be found in copending U.S. patent application Ser. No. 14/819,817, Ser. No. 14/819,851, and Ser. No. 14/819,889, the disclosures of which are incorporated herein by reference.

The example shows a cardiac electrical signal at 100, stored in a buffer of length M. The buffer length may be, for example, from about one to about ten seconds, with four seconds serving in several illustrative embodiments. About one half of the buffer has been extracted as a "comparator", shown at 102. The comparator 102 may be shorter than one-half the buffer length in other examples.

The comparator 102 is repeatedly compared using, for example, correlation waveform analysis or difference of area subtraction, for example (or other comparative technique) to a segment of equal length from the buffer 100. Each comparison occurs at a lag depth that begins at zero, and increases until the comparator 102 has been drawn across the buffer 100 to a desired extent. For example, supposing the buffer 100 contained 512 samples of data (four seconds at 128 Hz), and the comparator contained 256 samples of data (two seconds at 128 Hz), then the comparator could be subtracted at lag depths from 0 to 256, to yield 256 data points as shown below at 106, where each data point is calculated according to the formula shown at 104. The set of data points is referred to as $R[n]$, with n indicating the lag depth. As seen at 106, a first peak appears at the lag depth of 0—at this point, the comparator 102 is actually compared to itself, yielding a perfect match valued at 1.0 in the chart 106.

As the lag depth increases, the match decreases quickly from the initial perfect match. As the lag depth continues to increase, a peak appears at 112. This peak corresponds to a lag depth illustrated at 120, in which the R-wave peaks in the comparator 102 each line up to R-wave peaks in the buffer 100. As the calculation occurs to the larger lag depths, a set of peaks emerges as shown at 112, 114, 116, with each peak appearing at a lag depth where the ECG signal peaks 100 line up with respective peaks in the comparator 102.

The next step is to determine which of the peaks in the graph 106 provides a best estimate of cardiac rate. An illustrative rule set would first throw out the peak at 110, as it is an artifact of the comparison at Lag=0. Next, peak 118 may be ruled out as being too short, using as an example a requirement that $R[n]$ (formula 104) exceed a threshold that can be set in the range of about 0.3 to about 0.5 for peaks to be considered. Finally peak 112 may be selected at the peak with the shortest lag time that exceeds the height threshold. Peak 112 may be confirmed as a high confidence estimate by determining whether one or more of peak 114 and 116 are an integer multiples of the lag depth of peak 112. These integer multiple peaks 114 and 116 are referred to as "Pickets" in copending U.S. patent application Ser. No. 14/819,817, Ser. No. 14/819,851, and Ser. No. 14/819,889, which provide numerous additional examples and detailed discussions.

The lag depth can be converted to a cardiac rate if the sampling rate is known. For example, a lag depth of 64 samples, at 128 hertz, gives a period of 500 milliseconds and converts to 120 beats per minute. In the example shown, if the data is obtained at 128 Hz, and peak 112 is at a lag depth of about n=85, the corresponding period would be 664 milliseconds (85 times 7.8 milliseconds), converting to a rate of 90 BPM. It may be noted, for confirmation of this summary explanation, that the four second buffer 100 has six sharp R-wave peaks in it, corresponding to 90 BPM.

At least two features should be noted with respect to FIG. 4. First, rather than finding individual cardiac cycles, the method identifies lag depths of greatest similarity of the comparator 102 to the ECG 100. Therefore the outcomes are likely to be independent of an analysis that uses individual cycle detection. Second, there are measures of confidence that can be gleaned from the graph at 106—one measure is a very high peak ($R[n]$ of 0.6 or above, for example) which will suggest a very high match between comparator 102 and buffer 100 at some lag depth, and an accurate lag depth from which rate may be calculated. Another confidence measure is the presence of pickets at integer multiples of the selected peak—here, peak 112 would be at a lag depth of about n=85, and peaks 114 and 116 would be at lag depths of about n=170 and n=255, respectively.

The method illustrated in FIG. 4 may be repeated at intervals, for example, at intervals of 500 milliseconds to 10 seconds, or more or less, as desired. If the rate found in successive iterations is similar, this also adds to confidence in the outcome.

Thus there are at least three measures of confidence in the method of FIG. 4:

Peak height

The existence of "pickets"—additional peaks at integer multiples of the lag depth of a peak Repeated similar outcomes Rate estimates can thus be graded according to confidence, from high confidence if two or three of these factors (or other factors) are present, to low confidence if only one of the factors is present. Confidence may be used in determining which of multiple rate measurements to rely upon in making therapy decisions and at other places in the following methods, as described below.

It can also be observed that the rate calculation shown in FIG. 4 requires a large number of computational steps—such as the repeated subtractions of blocks of data used to generate the function $R[n]$. Many patients with active implantable cardiac devices spend most of their days and nights experiencing normal sinus rhythm at benign rates in the range of 50 to 100 bpm. Intensive rate calculation is not necessary during these times and could cause unnecessarily short battery life for such devices (assuming non-rechargeable batteries), or may necessitate inconvenient and frequent recharging sessions (if rechargeable batteries are used). Therefore several illustrative devices and methods below are directed toward decision processes that can turn on the more computationally intensive rate calculation only when needed.

Figure 5:
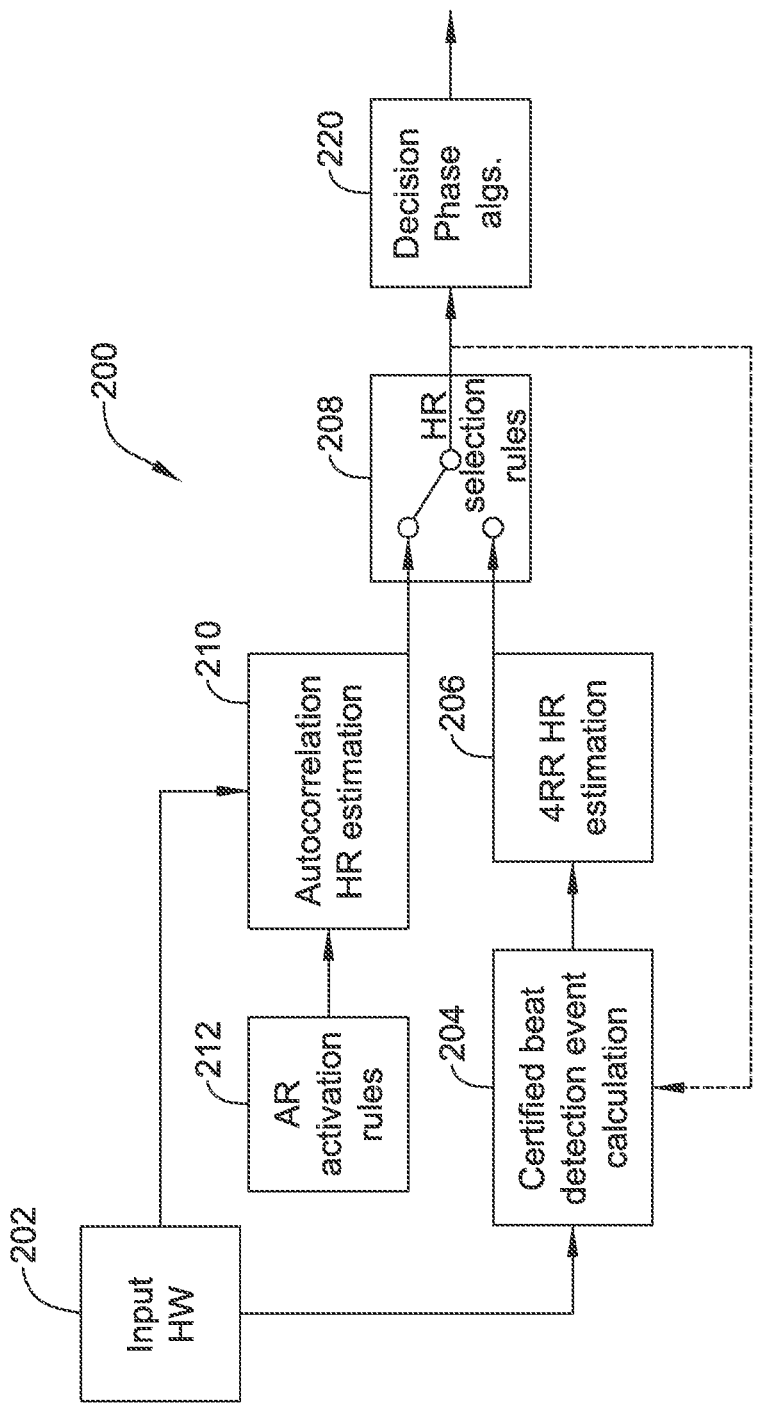
FIGS. 5-7 show illustrative methods in block flow form.
Figure 6:
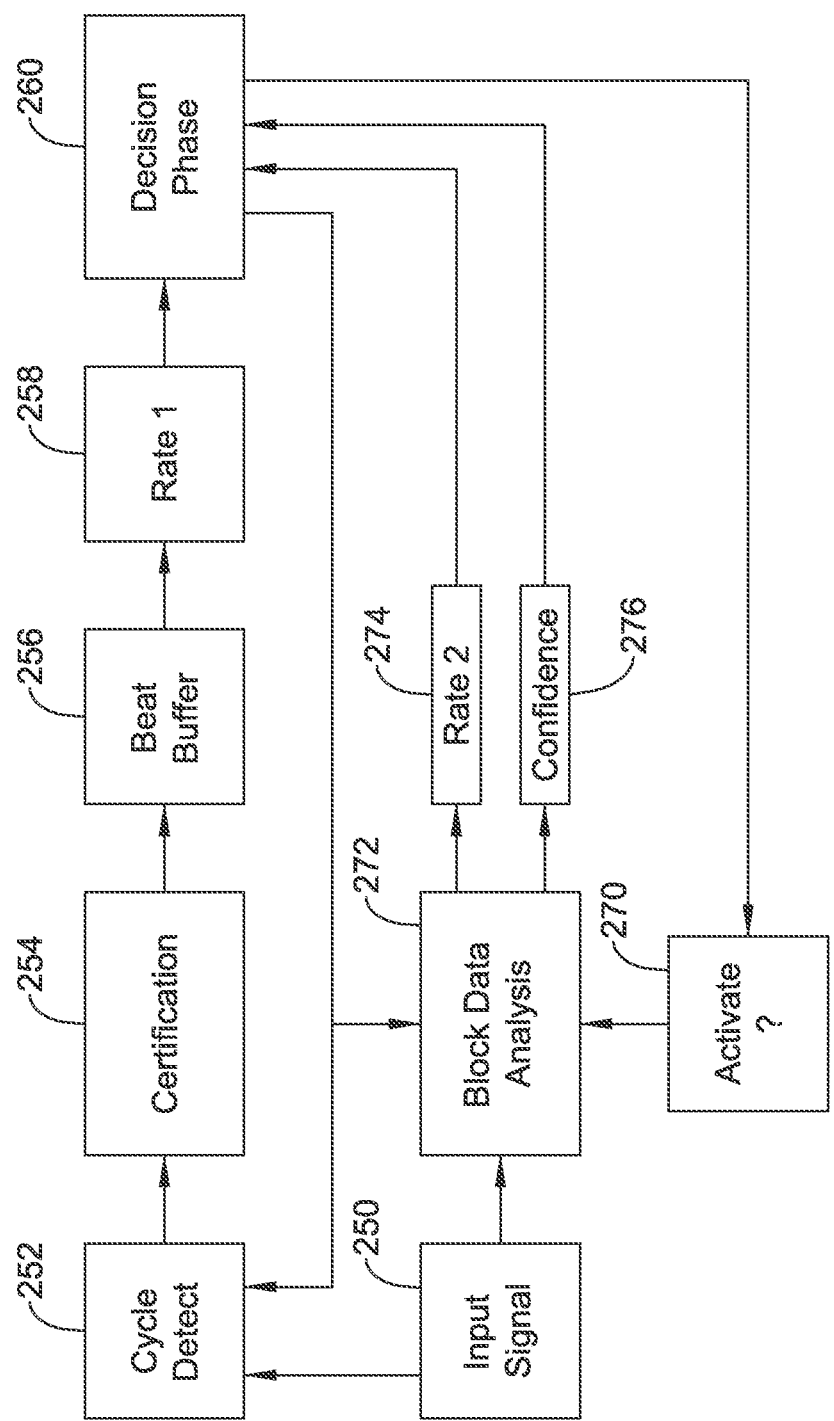
Figure 7:
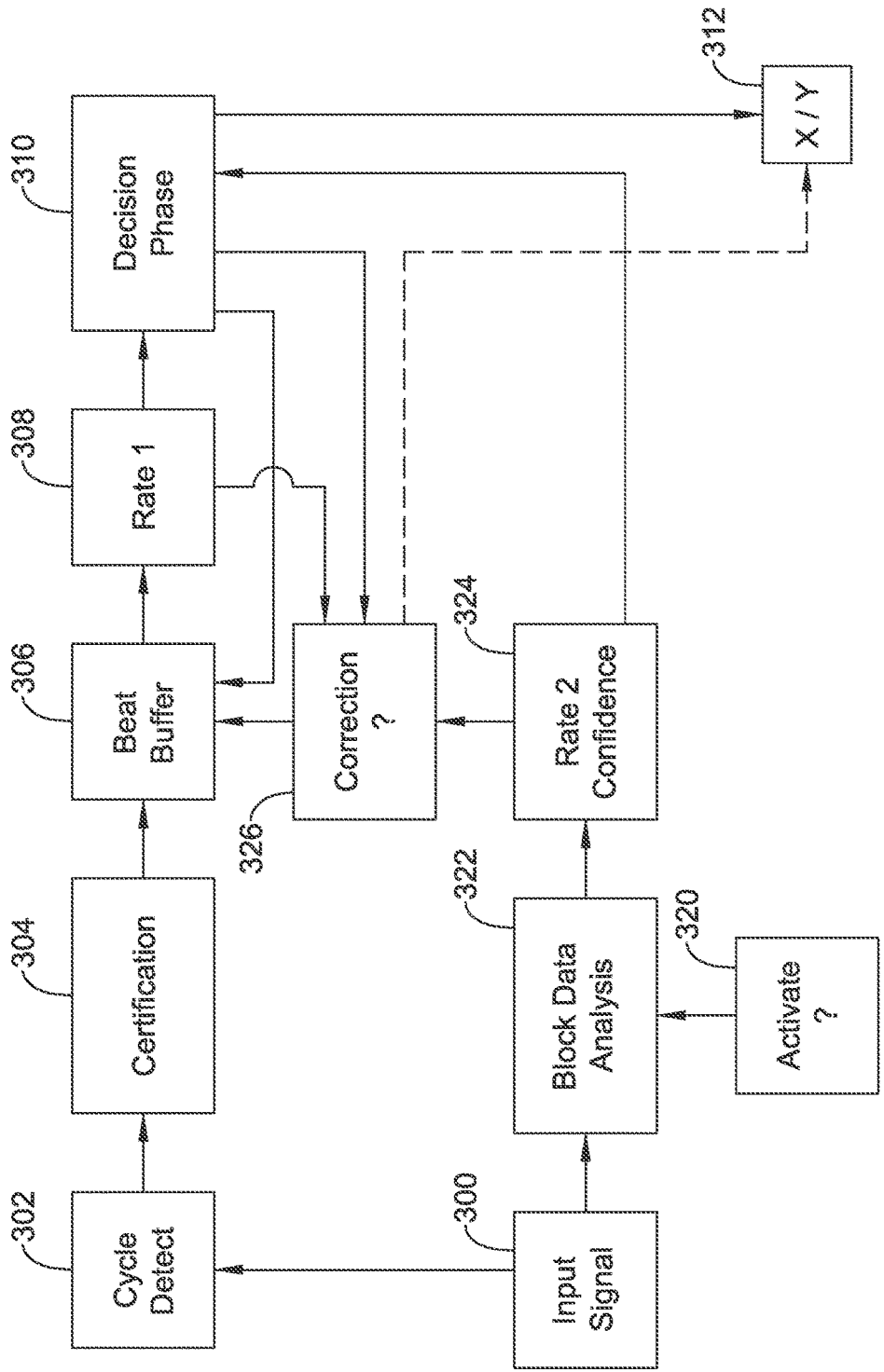

FIGS. 5-7 show illustrative methods in block flow form. In FIG. 5, the method 200 starts with an input signal 202 which may come from the device hardware, such as an input block comprising DC filtering capacitors, one or more amplifiers, and sense signal selection switches (or a multiplexor) for those devices having multiple available sensing vectors, for example. The input signal 202 in this example is a cardiac electrical signal. In other examples, other signals, such as those from sensors for one or more of blood pressure, heart sounds, respiration, motion, pulse oximetry, chemical/chemical changes, etc., may be included.

The signal is passed to a cycle-detection based processing sequence, as noted at 204. The cycle-detection sequence 204 may include, for example, cardiac cycle detection and certification of detected cycles, as indicated at 204. From the certified detected cycles an average interval is calculated at 206, which may be, for example, an average of four intervals between certified cycles or R-waves, for which "4 RR" is a shorthand. Other waves of the cardiac cycle may be detected, in different quantities, as desired.

A heart rate selection block is shown at 208. Block 208 may select between the rate from block 208 and a rate determined by use of an autocorrelation function 210, and passes the result forward to a decision phase 220, which may be much as described above relative to FIG. 2. The decision phase 220 may further perform data correction described below to change stored rates or detected events or the X/Y filter contents, among other modifications, when using the second cardiac rate estimate from block 210 instead of or in addition to the first cardiac rate estimate from block 206.

The autocorrelation function 210 may be performed periodically or in response to detected conditions, based on a set of autocorrelation activation rules noted at 212. The autocorrelation analysis may be as disclosed in one or more of U.S. patent application Ser. No. 14/819,817, Ser. No. 14/819,851, and Ser. No. 14/819,889, which provide numerous additional examples and detailed discussions. FIG. 4, above, provides a summary level view of an autocorrelation function.

It should be noted again that the rate estimate from block 210 may use an analysis other than autocorrelation. For example, a device as in FIG. 1 may communicate to a second implantable device, such as a subcutaneous monitor, a transvenous pacemaker, or a leadless cardiac pacemaker implanted inside the heart, to obtain a rate therefrom. See, for example, US PG Patent Application Publication 20150196758, titled SYSTEMS AND METHODS FOR DETECTING CARDIAC ARRHYTHMIAS, the disclosure of which is incorporated herein by reference. Other examples may rely on a different data type, such as blood pressure data, pulse oximetry, cardiac motion, or heart sounds, for example, to determine or estimate cardiac rate, where the sensor for the second rate may be part of the same device as is performing the analysis of FIG. 5, or may be provided by a separate device located elsewhere in the patient's body, with the rate obtained using wireless or tethered communication, or by conducted communication through the body.

Some illustrative rules for activation at block 212 may include the following:

- A finding that the rate calculated at block 206 is above a threshold, either in a single measurement or repeatedly.
- A finding that an X/Y filter used in a device has reached or crossed a threshold.
- A periodic check of rate may be performed by, for example, activating the second rate block 210 as relatively long intervals (two to thirty seconds, for example) and comparing to the rate calculated at block 20. If the rates are different (for example, more than 10 to 30% apart, or off by at least 30-60 bpm), a shorter interval activation (500 ms to 2 seconds, for example) of block 210 may be initiated.
- A finding that noise or overdetection or a combination thereof is being observed. For example, if two consecutive detected cardiac cycles are found to be noisy or caused by noise and fail certification, or if three out of seven consecutive detected cardiac cycles are found to be overdetection and fail certification, or other similar boundaries.
- A long pause between detected cycles takes place.
- A change in signal quality for the signal generated by the input hardware 202, for example as described in copending U.S. Patent Application 62/245,757, titled SIGNAL QUALITY MONITORING FOR MULTIPLE SENSE VECTORS IN CARDIAC DEVICES, the disclosure of which is incorporated herein by reference. This may include a drop in signal amplitude or a change in signal spectral content, and/or other factors noted in the copending application.
- A comparison between cardiac cycle based rate counting and observation of an activity sensor output which shows a disparity. For example, patient activity can be tracked with temperature, motion, or other sensors; when the patient is active according to such sensors, but the observed cycle rate is low, or, alternatively, when the patient is inactive according to such sensors but the observed cycle rate is high, a disparity would be found.
- A determination that the patient has changed posture, where, for example, the change in posture may affect sensing signal quality and so a comparison of rate analyses can be useful.

In any of the above circumstances, a new activation can be applied, once, repeatedly for a preset time period, or repeatedly until some event occurs. Active engagement simply means sufficient availability to be used in the later decision phase at 220. For example, a second rate may be sufficiently active if results are provided at intervals of 500 milliseconds up to four seconds, or longer as desired; in some example, the second rate may be provided about once every 1-2 seconds. In some examples, such as after a change in posture, a single confirmation that the first rate calculation, based on detecting cardiac cycles, for example, continues to be valid, may be performed and so a single activation is made.

As noted, in some examples, activation may occur until an event takes place, such as expiration of a timer or one of the following:

- If the two heart rates provided at blocks 206 and 210 are similar
- If a condition, such as elevated rate or an X/Y filter in excess of a threshold, or an observed disparity between measures of activity and rate, no longer exists (for at least a minimum period of time in some examples)
- Assuming noise or overdetection was a trigger for activation at 212, if beat certification resumes consistent certification indicating an end to noise or overdetection
- Assuming a drop in amplitude or signal quality was a trigger for activation at 212, if the amplitude increases or signal quality improves The end of active engagement may entail complete disabling of the second rate calculation 210, or may indicate a longer period between iterations of the second rate calculation. For example, when "active", a second rate calculation may occur or be obtained at 500 ms to two second intervals; when inactive, the second rate calculation may occur or be obtained at longer intervals such as four to thirty seconds.

FIG. 6 shows another example. Beginning with the input signal 250, a cycle detection method is applied at 252, leading to certification phase 254. The outcomes from certification phase are used to populate a beat buffer 256, from which a first rate, "Rate 1" is calculated as indicated at 258. Rate 1 is then provided to the decision phase at 260.

In another data stream, the input signal 250 passes to a block data analysis 272, which performs analysis according to an activation schedule 270 and yields an output, Rate 2, at 274. Rate 2 may be associated with a confidence measure 276 as described above in reference to FIG. 4. The decision phase 260 may use the confidence 276 to determine which of Rate 1 or Rate 2 to rely upon.

The decision phase 260 may use analysis of Rate 1, or of the beat buffer 256, alongside Rate 2 274 and or confidence 276, for example, to determine whether to trigger more frequent activation 270 of the block data analysis 272. For example:

- If either Rate 1 or Rate 2 exceeds a predetermined threshold, and the confidence 276 is above a threshold, more frequent activation 270 may be called upon for a period of time until either the predetermined threshold is no longer exceeded, or the confidence 276 drops;
- If the decision phase determines that an X/Y filter has begun filling, or has reached a first threshold, more frequent activation 270 may be called upon until the filter X/Y drops below a second threshold, unless the confidence 276 is low; and/or
- If the beat buffer, which in one example may include both certified and not-certified cycle markers (including, for example, noise or overdetection markers), contains more markers for a period of time than would be predicted given Rate 2, more frequent activation may be called.
- Other examples noted above for de-activating, or reducing the frequency of activation, of a second cardiac rate measurement, may be used as well.

FIG. 7 shows another example. Here again, the input signal 300 goes through cycle detection 302 and certification 304 to populate a buffer 306. The buffer 306 can be used to calculate a first rate, Rate 1, 308 for use by the decision phase 310. The decision phase 310 may mark events in the buffer as treatable or non-treatable in this example; in the prior example of FIG. 6, the buffer may simply be a beat buffer indicating time stamps and, as desired, associated shape data for certified detected cycles. The decision phase 310 may keep a separate X/Y filter (or plural X/Y filters) for marking treatable or non-treatable indications.

Further in this example, an activation block 320 may trigger second rate calculation via block data analysis at 322 (though other second rate calculations noted above may instead be performed). The analysis at 322 yields a second rate, Rate 2, which may be associated with a confidence measure as noted at 324.

Figure 9:
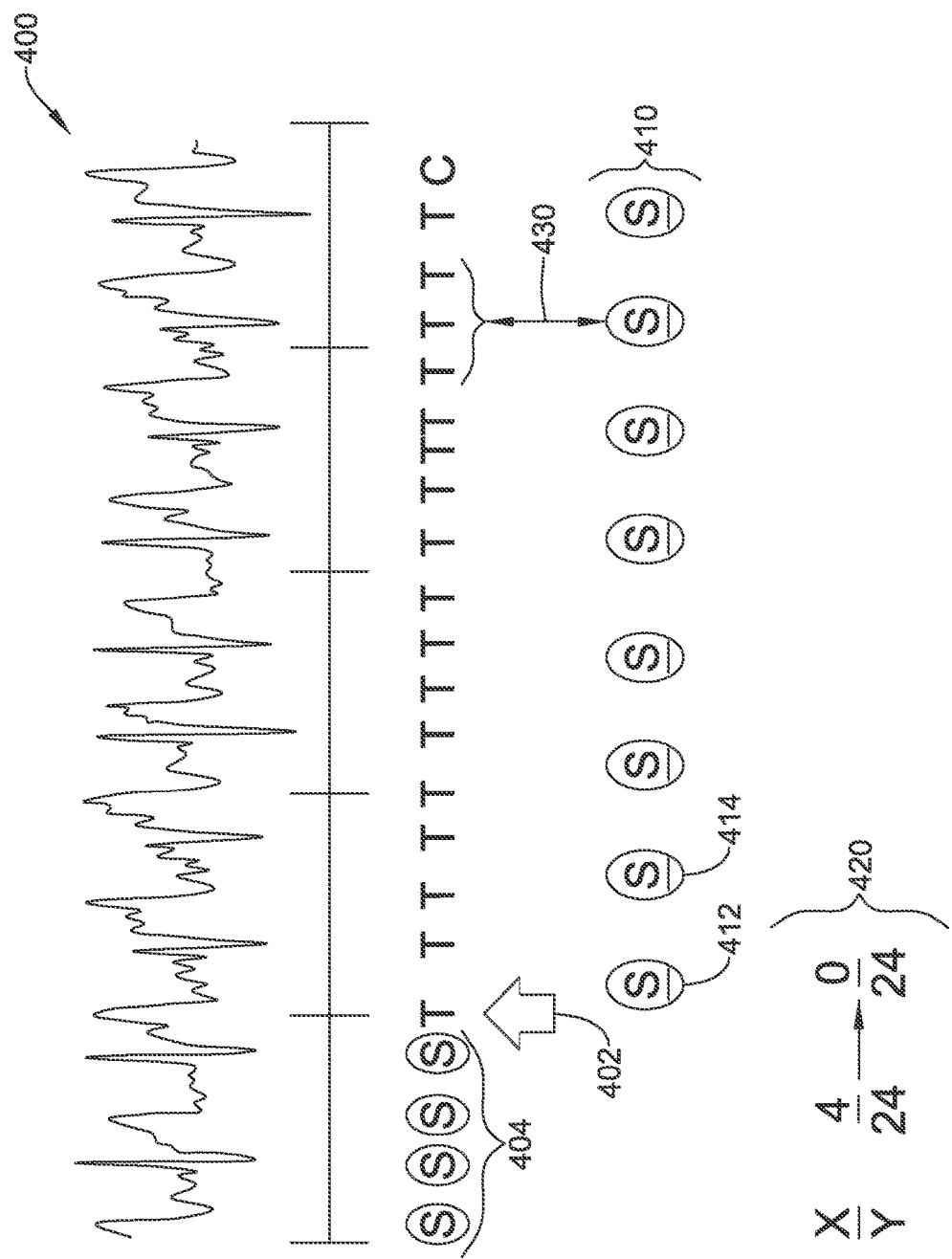
Figure 10:
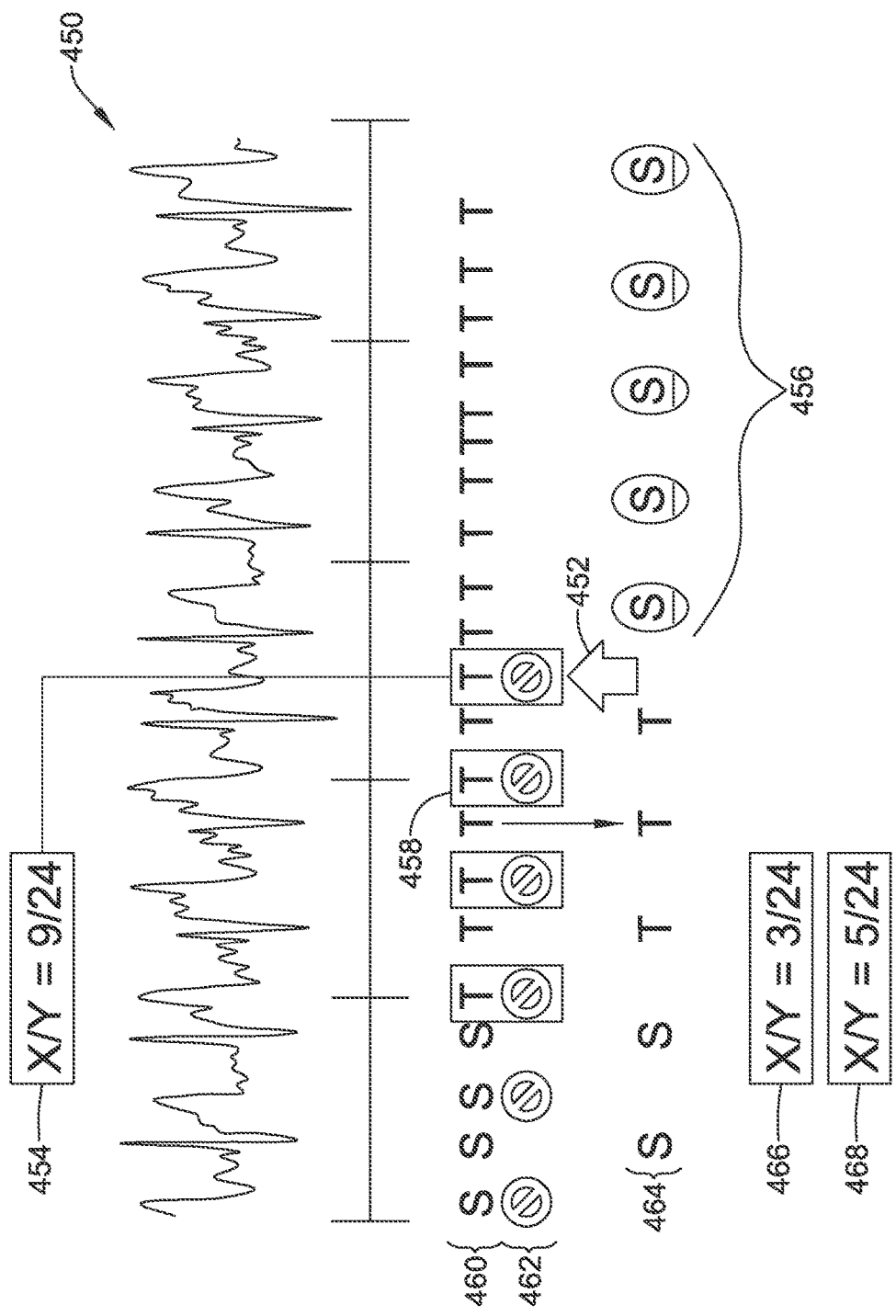
Figure 11:
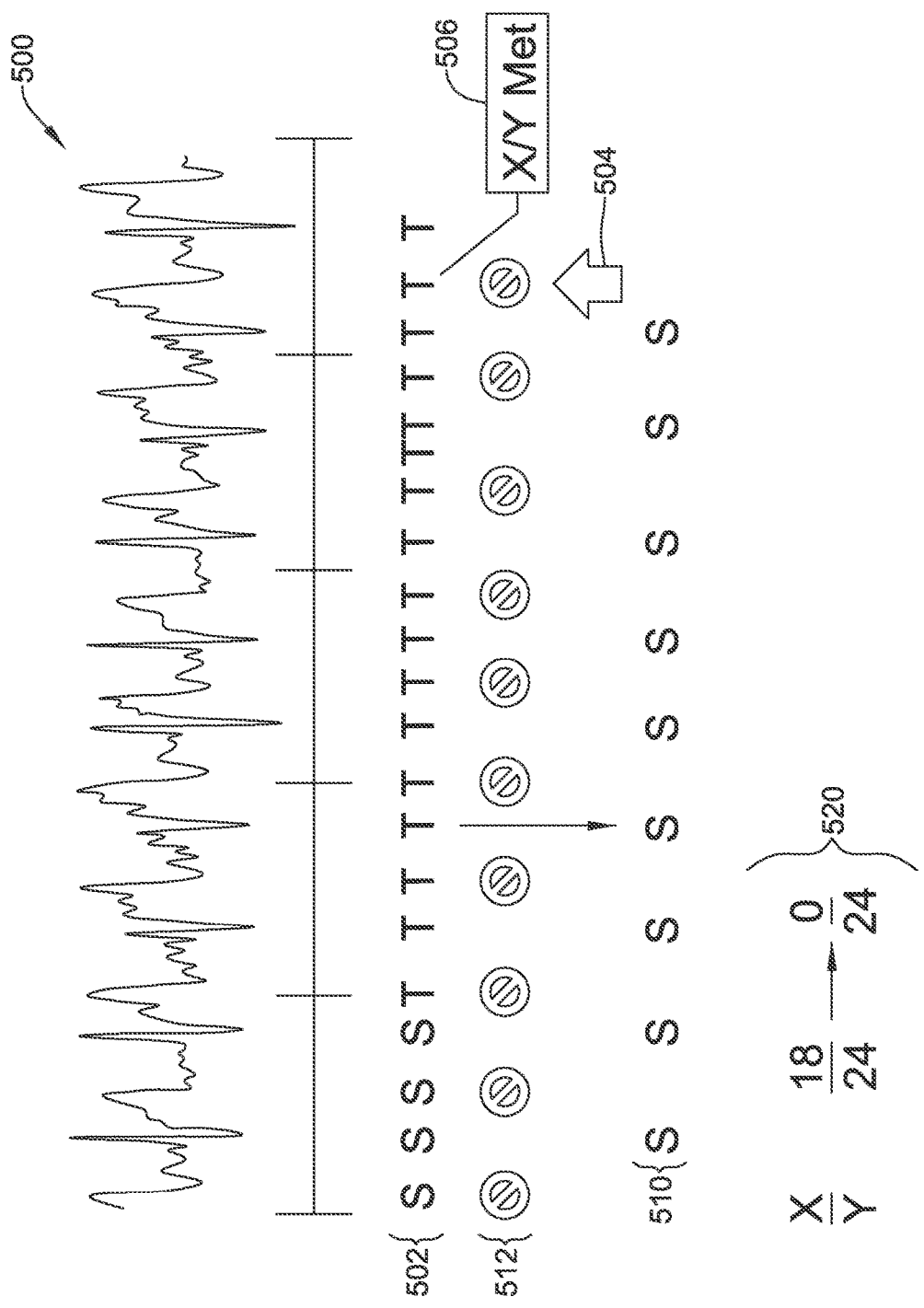

The decision phase 310, or a separate logic block 326, can decide whether correction is needed in response to a discrepancy between Rate 1 and Rate 2. Correction may take place using the beat buffer 306, or may occur on the separately provided X/Y filter, or both, as desired. Some examples of correction in the X/Y filter are shown in FIGS. 9-11, which demonstrate methods by showing cardiac signals and counter markers. Additional examples directed at the beat buffer 306 are shown in U.S. Provisional Patent Application 62/262,048, titled METHODS AND DEVICES COMBINING MULTIPLE CARDIAC RATE MEASUREMENTS WITH INTERVAL CORRECTION AND ARRHYTHMIA DECISION BYPASS, the disclosure of which is incorporated herein by reference.

Figure 8:
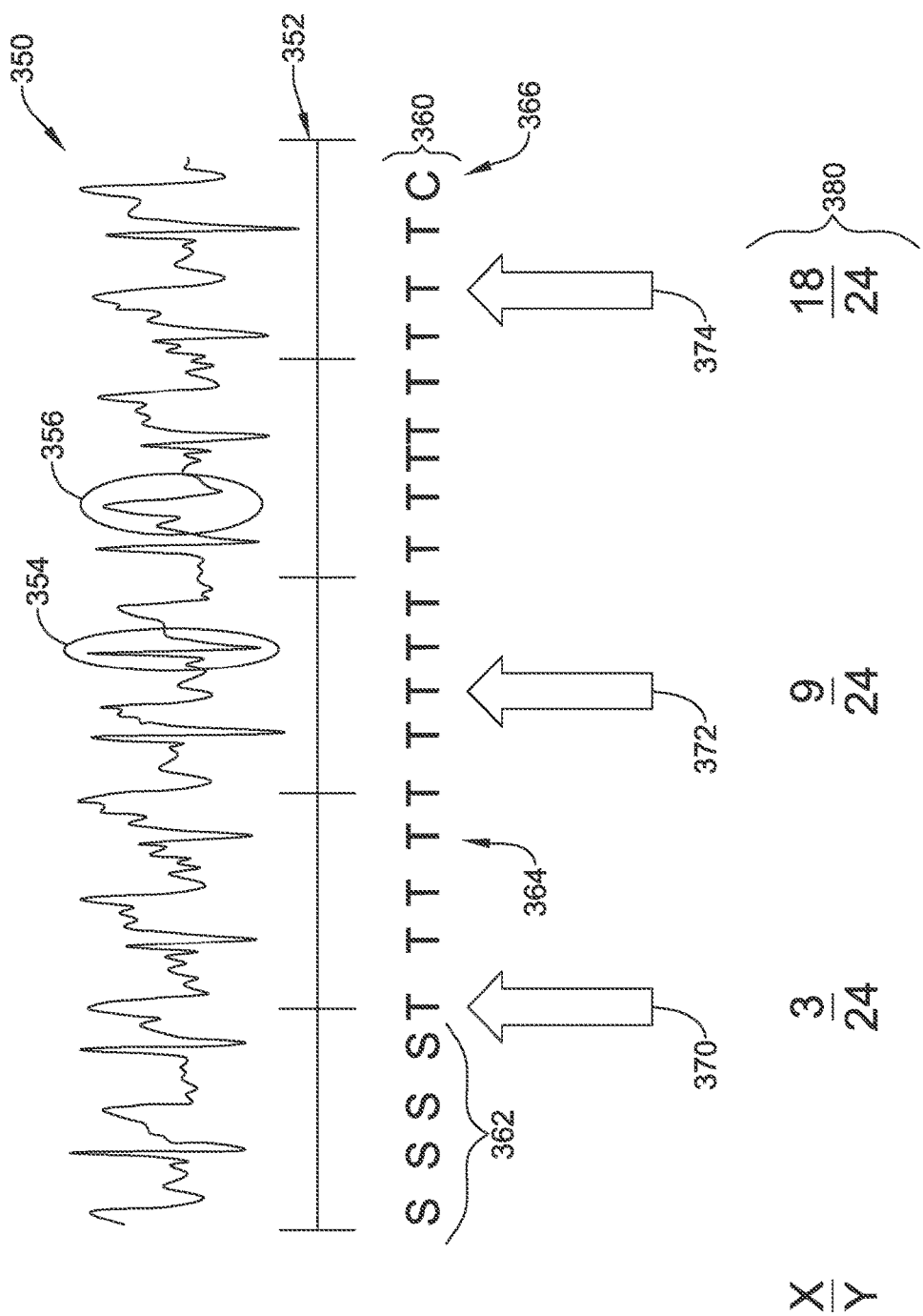
FIGS. 8-12 demonstrate methods by showing cardiac signals and counter markers.

FIG. 8 shows an illustrative example without a second rate analysis or data correction. A cardiac electrical signal is shown at 350 along a timeline 352 with major tick marks shown at one second intervals for illustrative purposes. R-waves or QRS complexes are relatively sharp biphasic peaks in the signal 350 such as that shown at 354, while T-waves are generally wider as shown at 356; it may also be noted that the T-waves 356 in this drawing are generally monophasic in contrast to the biphasic R-waves 354.

The letters shown at 360 are used for counting in an X/Y filter, with the S-markers counting as zero, and the T-markers counting as one; additional rules may be built into the X/Y filter calculation if desired. In the example one may assume the signal was correctly detected off to the left of the figure and only began showing malsensing and increasing rate at 362. Thus the markers at 362 include four S-markers, each indicating a slow rate calculation has occurred. It can be noted from 350 that there are only two sharp R-wave peaks in a corresponding signal in the time that four S-markers appear at 362. This makes two of the four markers at 362 T-wave overdetections.

With four markers in one second at 362, the calculated rate would rise quickly above most tachycardia thresholds used in the art; for example, the threshold may be user defined or pre-set in a range of about 140 to 240 beats per minute. As a result, starting at 370, the markers 360 become T markers, as shown at 364. In one example, line 370 may be a trigger for performing or obtaining a second analysis of rate.

The counted outcome for the X/Y filter is indicated at 380. In this example, the X/Y filter is set to 3/24 with the first T-marker at 370, to account for the fact that the new T-marker represents a four-RR average meaning that more than a single detected event occurred at a tachycardia rate. In another example, the X/Y filter may actually count only the T markers, so it would start at 1/24. In yet another example, the X/Y filter could be more aggressively set to 4/24 upon the first T after a string of S-markers.

Six detections later, at the arrow 372, the X/Y filter has reached a value of 9/24, which in this example is half-way to reaching a therapy threshold of 18/24. In some examples, reaching halfway to the X/Y filter threshold may be a trigger for activating or obtaining a second cardiac rate calculation. Still later, at 374, the X/Y filter threshold of 18/24 is reached, providing a third potential trigger point for activating or obtaining a second cardiac rate calculation in some examples. Other trigger points may be used instead, for example, counting a quantity of consecutive T-markers, or a number of detected events of any type in a window of time (such as four cycle detections in one second). In other examples, different thresholds for both X and Y may be used, as well as the trigger points.

In this example, a two-event persistence threshold is applied, calling for the X/Y filter to stay at or above 18/24 for at least two consecutive iterations, where the X/Y filter is applied on a first-in, first-out basis, before capacitor charging begins as indicated by the C-marker at 366. The C-marker may, for example, reset the X/Y filter until therapy is delivered or the patient is found to have returned to normal cardiac rhythm. Capacitor charging indicates preparation for high power therapy delivery.

FIG. 9 uses the data of FIG. 8, but now instead makes reference to a second rate calculation. In this example, again, the cardiac signal is shown 400 and the detected cycles at 404 cause the rate calculation using cycle detection to cross a tachycardia threshold, as indicated at 402. As shown at 420, the crossing to tachycardia causes the X/Y filter to be seeded, this time to a value of 4.

Further in the example of FIG. 9, the second rate calculation triggered at 402 finds a different, slower rate, than the cardiac cycle detection method could find. The second rate calculation may use, for example, the data block method such as autocorrelation shown above in FIG. 4 or may instead be generated using pulse oximetry, spectral analysis or various other methods noted above, or may be obtained by querying a second device. The second rate calculation can then be substituted for the first rate calculation as indicated at 410 by synthesizing "detected" cycles at 412, 414. These synthesized detections are used to fill data buffers, such as one or more of an X/Y filter and/or a beat buffer. For those examples where the second rate calculation is accompanied by a confidence measure, inclusion of high confidence may be a predicate to the data changing noted at 410 and/or a reset of the X/Y filter that is also noted at 420.

The second rate calculation is repeated at appropriate periods until it is deactivated or returned to a less active state—for example, and referring to FIG. 4, if the signal buffer 100 held four seconds of data, and the comparator 102 held two seconds of data, then the second rate calculation would be called at intervals in the range of about one to about two seconds. In some examples, the longest duration ensures that data is used at least once in the comparator 102, and the shortest duration ensures that data is not used more than twice in the comparator. Other longest or shortest durations may be used, as well as other durations for the signal buffer 100 and comparator 102, as desired.

Referring again to FIG. 9, the analysis may continue to compare the cycle-detected markers to the synthesized markers 410, as indicated at 430. The second rate analysis, in this example, may remain active until the cycle detected rate calculation matches the rate calculated by the second rate analysis. The synthesized markers 410 may be generated at a rate matching the second rate calculation, but may not actually appear in alignment with the R-waves in the signal 400. Therefore comparison at 430 may be a time-block comparison using, for example, one to four seconds of data and comparing the number of detections in the cycle-detection data to an expected quantity from the second rate calculation.

Also in FIG. 9, there are multiple ways that the X/Y filter may be handled. In this example, the X/Y filter is reset to 0/24 as soon as the discrepancy between the cycle-based rate and the second rate calculation is found. In another example, the X/Y filter may be filled with non-treatable indicators using the synthesized marker 410, such that older data (which may have set the X/Y filter to something other than 0/24) is pushed out of the X/Y filter at a rate matching the second rate calculation.

FIG. 10 shows another example. The signal 450 and marker string at 460 is again the same as in FIG. 8. In this example, the second rate calculation is triggered/activated at 452 upon the X/Y filter reaching a threshold. In the example, the X/Y filter threshold is 9/24 or half-way to an 18/24 threshold, as indicated at 454. Forward looking, the rate calculations are synthesized again as shown at 456 following the trigger.

In the example of FIG. 10, the event marker buffer 460 and hence the X/Y filter, is also modified in a backward looking manner using the newly calculated rate. In one example, the newly calculated rate is used to count, by intervals or by blocks of time, to identify how many markers in the event marker buffer 460 should be omitted in order to attain a correct rate; the assumption is that the data used for the second rate calculation was captured during the time that these very markers were generated by a cycle detection method. The markers at 462 indicate those cycle detections that would have to be eliminated to reduce the number of detected cycles to the "right" quantity using the newly calculated rate from the second rate analysis. In one example, the cycle lengths are added together to identify those cycles that "should" remain in place, having intervals therebetween that match the corrected rate. Some examples for such analysis are shown in U.S. Provisional Patent Application 62/262,048, titled METHODS AND DEVICES COMBINING MULTIPLE CARDIAC RATE MEASUREMENTS WITH INTERVAL CORRECTION AND ARRHYTHMIA DECISION BYPASS, the disclosure of which is incorporated herein by reference.

This leaves a set of subtractions/corrections 462, leaving a reduced marker set, as indicated at 464. In a first example, the reduced marker set is then re-analyzed, with buffer seeding ignored, to leave 3 T-markers. This results in an X/Y filter content of 4/24, shown at 466. In a second example, the analysis counts how many marker deletions occur—that is, the markers at 462 are counted, and the total is subtracted from the X in the X/Y filter. This approach happens to again result in an X/Y of 3/24, as indicated at 466. In a third example, the analysis counts only those deletions that affect T-markers. Here, there are four T-makers discarded, as indicated in boxes 458. The X/Y counter value is reduced by four, to 5/24 from 9/24, as indicated at 468.

FIG. 11 shows yet another example, again starting with the data from FIG. 8 and signal 500. The original marker set is shown at 502. In this instance, the trigger point 504 for a second rate calculation to be performed or obtained is when the X/Y filter threshold is met, as indicated at 506. This example may be performed in a system that requires persistence in which the X/Y filter would have to be met, and stay met, for some quantity of iterations such as 1-20 iterations (or more).

The newly calculated rate is used to determine a "proper" number of detections for the time period shown spanned by the figure, as indicated at 510. Alternatively, a different period for the re-analysis may be used. For example, if the second rate calculation uses a block of data spanning a period of time, the backward looking data correction may be limited to the time period corresponding to the block of data.

Interval analysis may be used to select which of the marker set 502 to retain. For example, the logic associated with a correction step may be used to determine whether addition of intervals between detections in the set 502 will yield intervals that match the re-calculated rate and, if so, detected events are eliminated at 512 to yield a best-fit set of detections. Alternatively, a synthesized, uncoordinated set of markers may be generated instead.

Once a reduced set of detections is generated at 510 (or, as noted, in the alternative, a set of synthesized cycle detections is generated), the intervals/average intervals are assessed against a tachycardia rate threshold. In this example, the result includes both reducing the number of markers, and changing the remaining T-markers to S-markers. The X/Y filter can then be recalculated, as shown at 520. In this example, the X/Y filter is reduced from an 18/24 state to a 0/24 state.

By manipulating the X/Y filter, not only the "current" rate reset to a correct level, but the data loaded into the system is adjusted to reduce a risk of inappropriate therapy in the event that the second rate calculation becomes unavailable or drops in confidence suddenly. For example, if the second rate calculation in FIG. 11 was triggered at 504, with X/Y at 18/24, in only a forward looking manner, several cycles would have to pass before the X/Y filter could begin counting down.

Returning again to FIG. 8, there are additional opportunities between time 374 and charge begin 366 for triggering a second rate calculation. For example, the meeting of an X/Y filter threshold may be used to trigger low power therapy such as drug release or anti-tachycardia pacing (ATP). For example, since ATP is low power and generally pain-free to the patient, the process may favor ATP delivery. As a result, a second rate calculation may wait until after ATP is delivered to determine if therapy is still needed. In one example, point 372 triggers ATP, which lasts for one second, and, following passage of two more seconds of time, the second rate calculation is called upon to analyze the two seconds of data captured after the ATP was delivered. If the second rate calculation after ATP does not create doubt about the accuracy of detections prior to arrow 274, charge begin 366 is called.

Other examples combining ATP and a second rate calculation prior to charge begin 366 may be used instead. For example, the second rate calculation may be called both before and after ATP, such that it is used to confirm ATP and again to confirm charge begin 366. Any time the second rate calculation has a high confidence and a rate below a threshold, therapy can be withheld and therapy preparations stopped. Moreover, as shown in FIGS. 9-11, the second rate calculation may be used to correct prior X/Y counter data.

Figure 12:
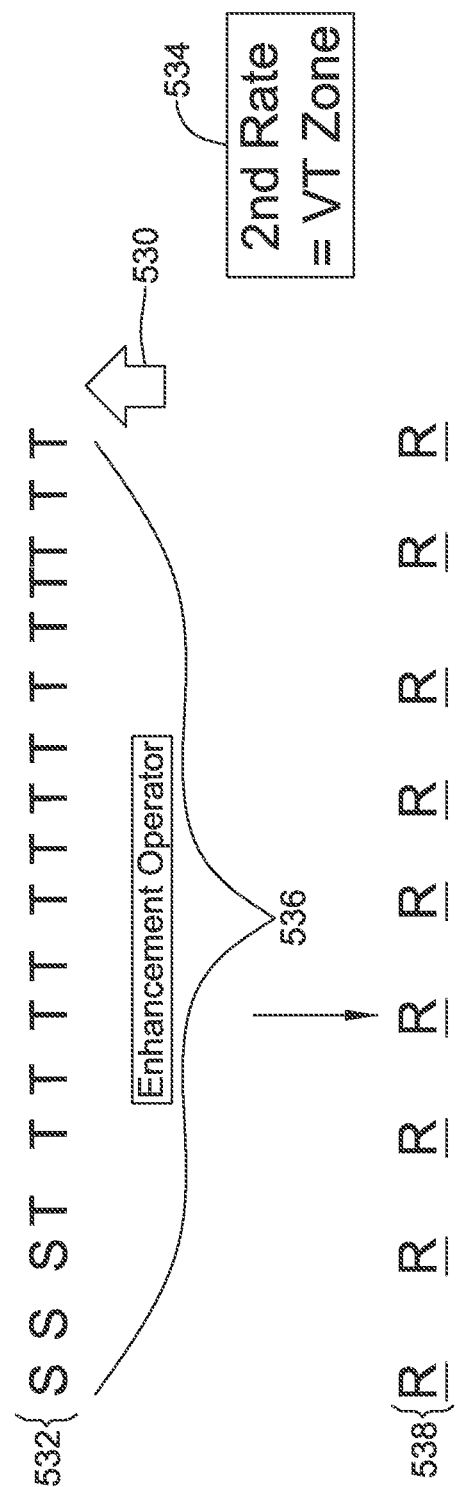

FIG. 12 provides another example, this time focusing only on the marker data. This example shows one way of handling an "enhancement zone" or VT zone. The use of an enhancement, discrimination or VT zone is illustrated in U.S. Pat. No. 7,330,757, titled METHOD FOR DISCRIMINATING BETWEEN VENTRICULAR AND SUPRAVENTRICULAR ARRHYTHMIAS, and also described briefly above. For such systems, the physician may set first and second rate thresholds to define a first rate boundary over which any detected event is considered treatable (the VF zone), and a second rate boundary below which any detected event is considered non-treatable. For detected events associated with rates between the first and second rate boundaries (the VT zone), secondary factors such as matching to a template, matching to adjacent beats, and/or R-wave or QRS complex width may be used to distinguish treatable from non-treatable detected events. The process can be referred to as VT/VF discrimination and may use "enhancement operators." The terminology may vary; in any event, a treat-only zone or VF zone is defined, and a discrimination, enhancement or VT zone is also defined.

If detection or counting errors push the rate into the VF zone, all detected events would be marked as treatable regardless how enhancement operators would work. To offset this issue, referring to FIG. 12, a second rate calculation is called at 530 in response to a marker buffer shown at 532. It may be assumed that the rate in marker buffer 532 is in the VF zone. The second rate, when called, is in the VT zone, where the enhancement operators would ordinarily be relied upon to discriminate shockable from non-shockable beats.

In the example of FIG. 12, in response to the VT zone rate being found, enhancement operators are applied to the detection represented in the marker buffer 532, as indicated at 536. Any results showing a non-treatable detected event using the enhancement operators are placed in the buffer 538 as results, R. If no non-treatable detected cardiac cycles are found in the set of events 532, all of the results, R, would in this example be T-markers. For example, the new detected rate results in this example in 8 slots available in set 538. If the individual detected events in block 532 include 5 cardiac cycles that match a stored sinus rhythm template (or meet some other enhancement operator such as narrow width or matching an adjacent detected event), then the newly calculated marker buffer at 538 would have 5 S-markers and 3 T-markers. In other examples, the newly calculated buffer could instead be filled with all S-markers, if the second rate calculation is of the nature shown in FIG. 4 and reports high confidence or high matching (R[n] peaks>0.7, for example), as the high confidence would indicated a monomorphic signal.

Figure 13:
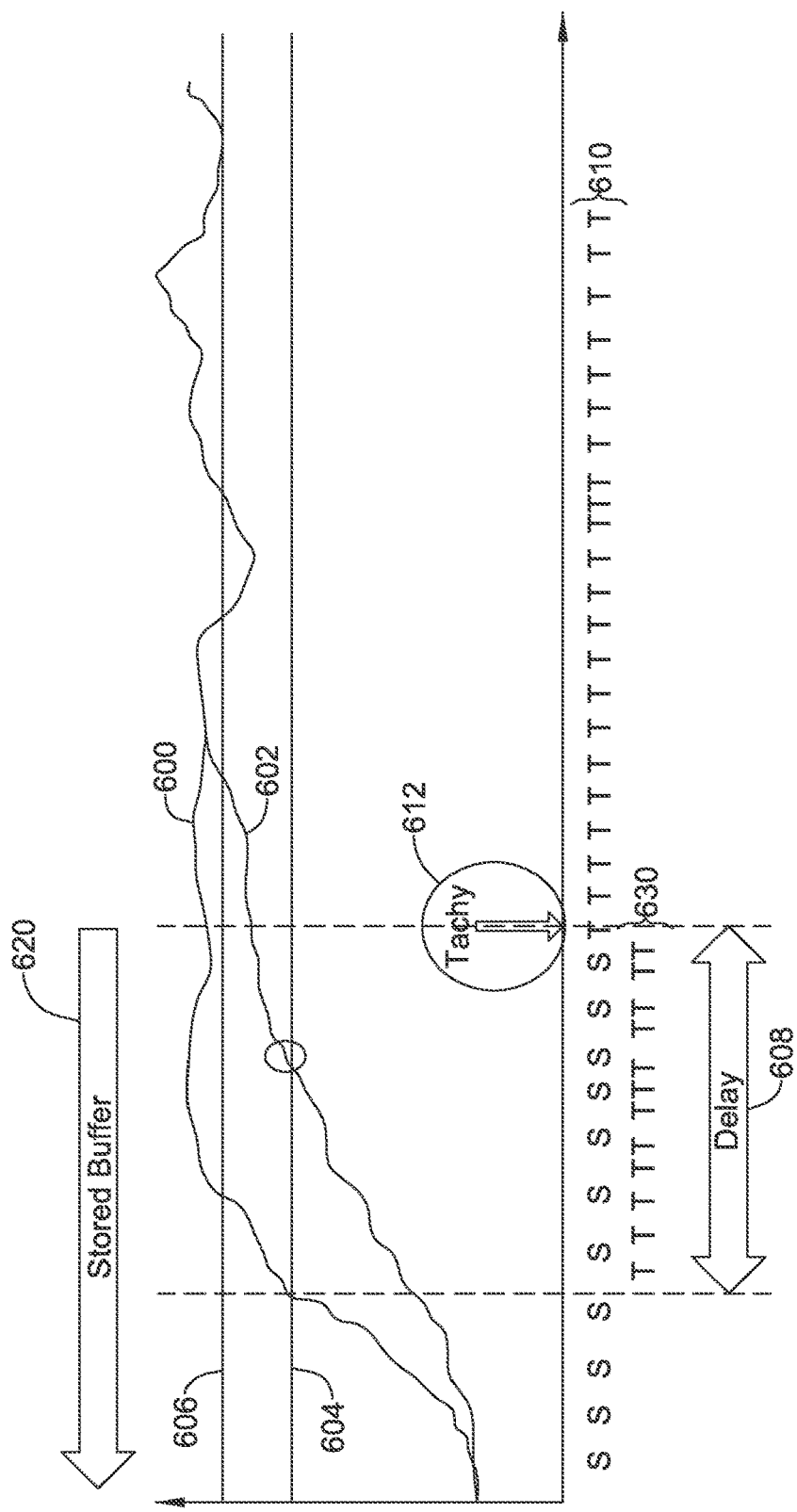
FIG. 13 shows an illustrative method for accelerating arrhythmia detection.

FIG. 13 shows an illustrative method for accelerating arrhythmia detection. A graph is shown with the true cardiac rate shown at 600 against a VT zone threshold 604 and a VF zone threshold 606, again using the enhancement or discrimination zone terminology. In this example, the cardiac signal is undersensed, causing the detected rate, which is shown at 602, to lag behind the true cardiac rate. This phenomenon can be observed when the onset of a treatable arrhythmia occurs with a drop in the average signal amplitude, as is not uncommon. The result is a delay 608 before the marker stream shown at 610 starts finding tachycardia, as indicated at 612.

In this example, the tachy declaration at 612 is used to trigger a second rate analysis calculation. Advantageously, in this example, a stored data buffer has been maintained as noted at 620. The existence of a stored buffer, which is often a circular buffer of a fixed size that keeps signal data in a first-in, first-out manner, is common in the art. For example, the S-ICD System shown in FIG. 1, above, in its first generation commercial embodiment, included a 44 second buffer of cardiac signal data. Larger or smaller buffers may be maintained.

In the example, the second rate calculation is performed, once triggered at 612, on at least a portion of the stored buffer 620 in addition to signal data as it comes in. Using the example of FIG. 4 as the second rate calculation, if the analysis in the second rate calculation covers four seconds of data, once flagged the second rate calculation would apply to four seconds of preceding data in the first instance, which may allow some data correction such as shown in FIG. 13. For further data correction, one or more additional analyses may be performed on stored prior data to reach back an additional two to six seconds, or more if desired.

The result here is that the second rate calculation is able to generate additional tachycardia markers as shown at 630. Such markers would be added to the X/Y filter, either by simply adding them or by recalculating the X/Y filter going back as far as the newly generated markers 630 go. The result is that the X/Y filter modified to fill it with indications of the treatable, high rate arrhythmia using the backward looking analysis. This may shorten the time to therapy in the event of an undersensing as shown in FIG. 13.

Figure 14:
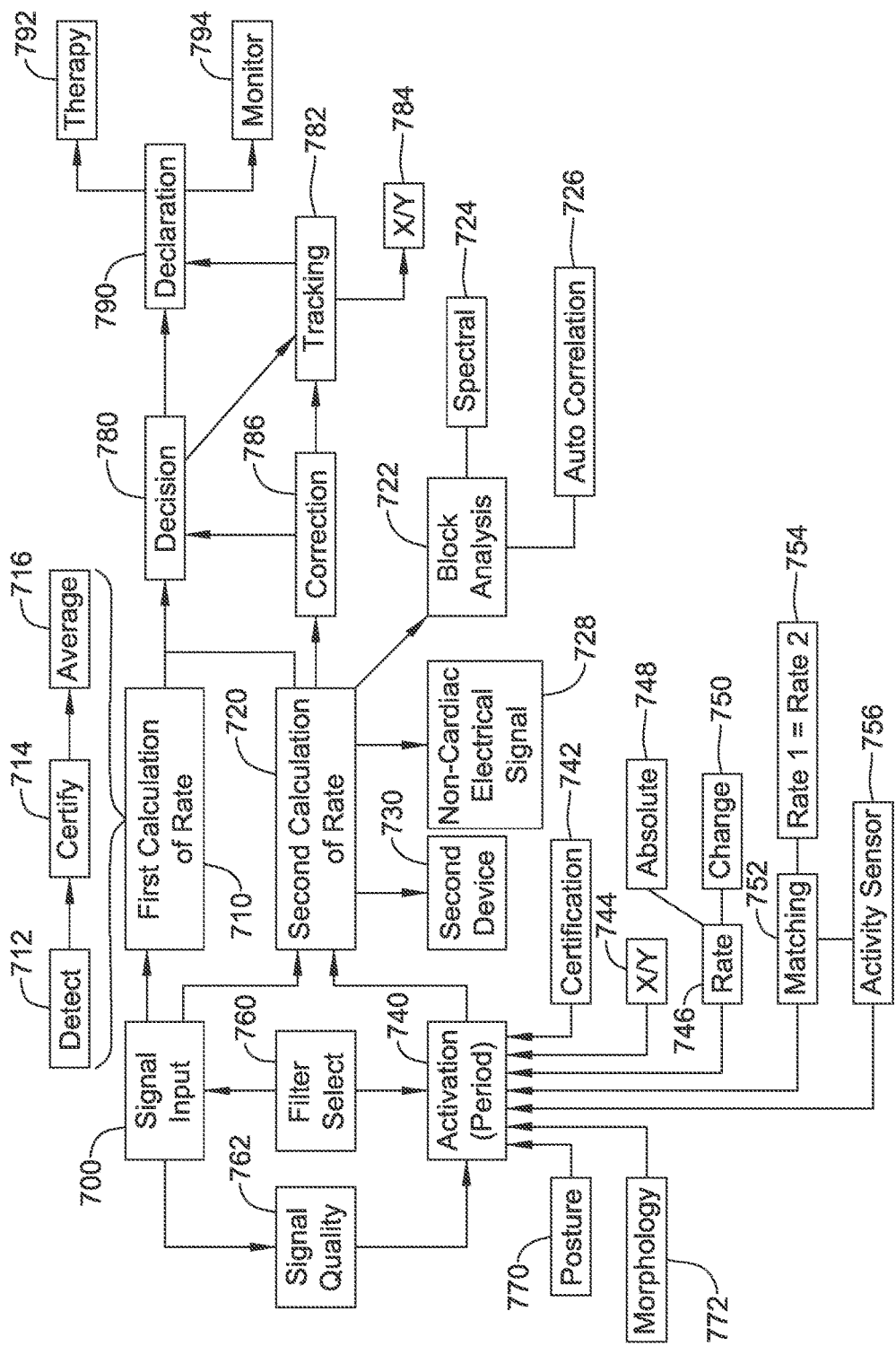
FIGS. 14-15 show illustrative examples in block form.
Figure 15:
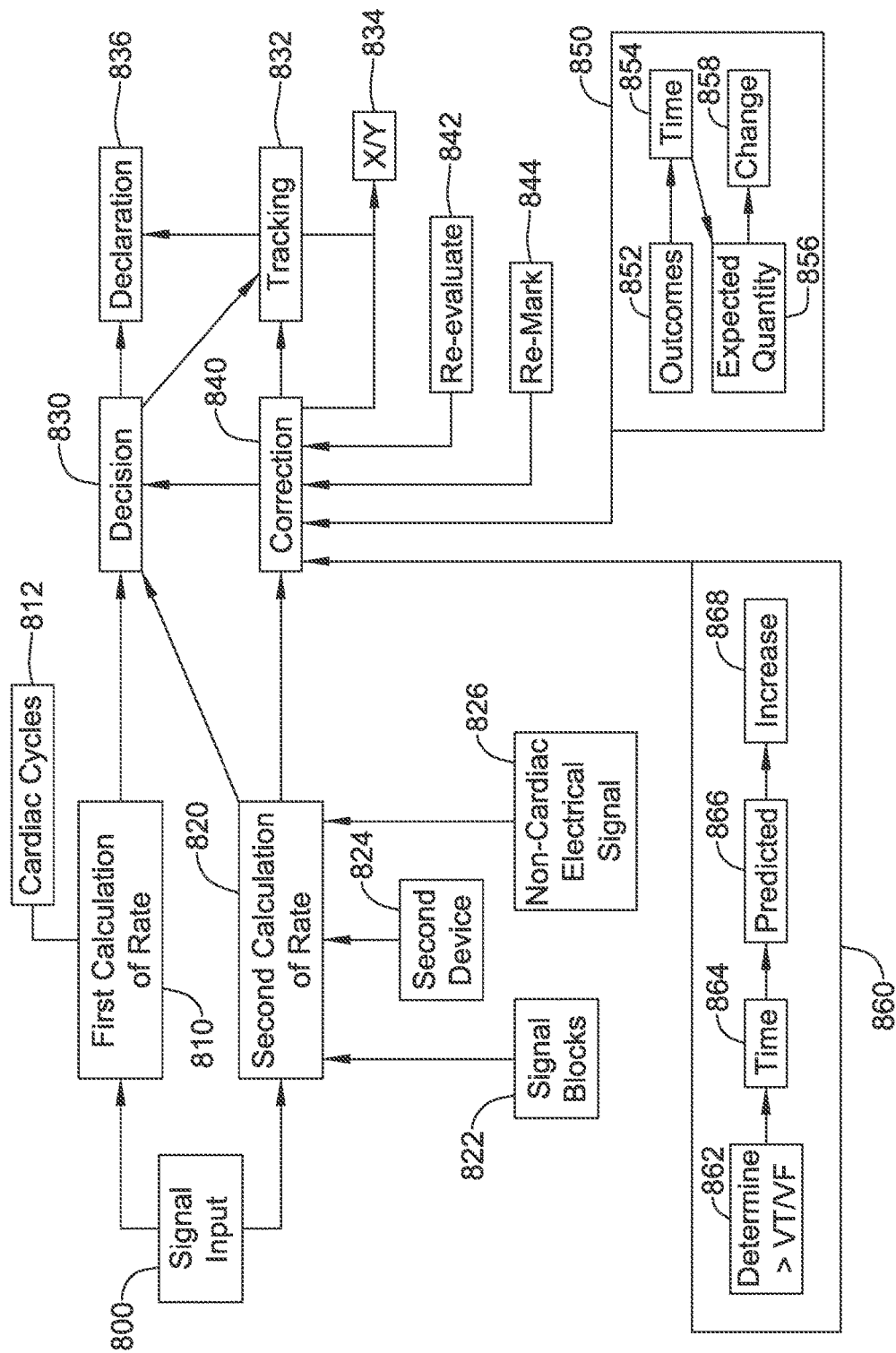

FIGS. 14-15 show illustrative examples in block form. Each block may represent a step in a method or may represent a dedicated circuit, set of instructions for operation by a processor or controller, or a combination of circuitry and instructions. Referring first to FIG. 14, it should be noted that several overlapping embodiments are shown in one image; various combinations of the blocks shown in FIG. 14 may be omitted and/or used in different examples.

In FIG. 14, a signal input block is shown at 700. The signal input block 700 may comprise, for example, switches for selecting a signal vector (if multiple sense vectors are available such as shown above in FIG. 1), filtering, amplification, and analog to digital conversion circuitry.

The signal input block 700 provides signal to a block for the first calculation of rate at 710. Block 710 may represent, for example, dedicated circuitry and/or executable instructions or instruction sets stored in memory for performing the detection of cardiac cycles at 712. Detected cycles from block 712 may undergo certification at 714. The certified cycles from block 712 may be used to calculate intervals which can be averaged at 716 to provide a first rate estimate that can then be provided by block 710 to a decision stage 780, explained below.

The signal input block 700 may also provide signal to a block for the second calculation of rate at 720. Block 720 may represent, for example, dedicated circuitry and/or executable instructions or instruction sets stored in memory for execution to provide several variants on the second calculation. Block 720 may operate using block data or signal analysis 722 using, for example, a spectral analysis 724, in which an average or peak spectral content may be determined for a block of data to yield a frequency of cardiac events. Block data or signal analysis 722 may instead use an autocorrelation function 726 such as that explained above with reference to FIG. 4 and/or copending U.S. patent application Ser. No. 14/819,817, Ser. No. 14/819,851, and Ser. No. 14/819,889, the disclosures of which are incorporated herein by reference.

Block 720 may, instead, rely on a non-cardiac-electrical signal, as indicated at 728—that is, the electrical cardiac signal may not be the focus of block 720. Some examples in block 728 may include the use of blood pressure data, pulse oximetry, cardiac motion, or heart sounds, for example. For such examples referencing block 728, the signal input 700 may provide a completely different signal to block 720 than to block 710. In still a further alternative, block 720 may obtain a cardiac rate estimate using a second device 730 such as by, for example, communicating with a second device that can provide a cardiac rate estimate. Some examples include, for example, a separate rate monitor such as a wearable or implantable cardiac monitor, pulse oximeter, blood pressure monitor, for example. In one example, a device having the functional and circuitry blocks illustrated in FIG. 14 may be an implantable subcutaneous-only defibrillator (such as shown in FIG. 1, above), and communication with a second device may include using wireless or conducted communication with a separate transvenous or intracardiac device such as a leadless cardiac pacemaker implanted in the heart.

The block for a second calculation of rate at 720 may use a computationally intensive or otherwise power hungry approach, meaning that keeping it active all the time may shorten battery life for a non-rechargeable battery powered device and/or require excessive recharging for a rechargeable device. Therefore in the example shown block 720 is activated by an activation block 740. As indicated, activation block 740 may, in some examples (particularly where block data analysis 722 is performed), periodically activate the second calculation of rate 720. The periodicity of block 740 may be varied from a relatively long period to a short period in some examples. In other examples, block 740 may be off or on, depending on one of several inputs. Each of changing the periodicity of block 740 to a shorter period, or directly turning block 740 on, can be considered activating the second calculation of rate block 720.

Block 740 is responsive to a variety of inputs (742, 744, 746, 748, 750, 752, 754, 756, 760, 762, 770, and/or 772). Various examples may use only one of the inputs shown, or may use 2, 3 or more in several combinations. Additional details on the inputs are provided below after the rest of the system in FIG. 14 is explained.

Blocks 710 and 720 may provide information to the decision block 780, where determinations are made as to whether or not a potentially treatable (for a therapy system, for example), or recordable (for a monitoring system, for example) cardiac rhythm or arrhythmia is occurring. The decision block 780 may rely on calculated or obtained cardiac rate measurements as well as cardiac signal morphology metrics such as template matching (to stored or dynamic templates and/or between near in time cardiac cycles), signal width, amplitude, or other measures. The decision block 780 may use a tracking block 782, which may comprise an X/Y filter, for example. In the example shown, if the rates output in blocks 710 and 720 diverge, a correction block 786 may be used to change the decision block 780 and/or tracking block 782 (including the X/Y filter 784). Various examples of the operation of a correction block 786 are illustrated above in FIGS. 9-13.

The decision block 780 and tracking block 782 provide information for a declaration block 790 which declares whether one of therapy activities 792 or monitoring activities 794 should be engaged. For example, therapy and/or therapy preparation may be commanded by block 790 via block 792 when the data provided to it satisfy therapy requirements. Data storage, alert annunciation, or message communication via block 794 may be initiated when monitoring thresholds are met. For example, the X/Y filter 784 may be required to reach a threshold (8/12, 12/16, 18/24, 30/40, for example), and the decision block 780 may be required to show that the most recently analyzed data supports a conclusion that an arrhythmia is occurring, and such conditions may be required to meet a persistence criteria, to satisfy therapy requirements. Other therapy requirements may be used.

In some examples, the second calculation of rate from block 720 may be used to overrule, or confirm, as the case may be, outcomes from block 710 in the decision block 780 and/or tracking block 782. As noted, however, block 720 may be selectively activated and/or activated at varying frequency/periodicity, in a process controlled via block 740, which may take a number of inputs:

In one example, block 740 may receive an input indicated at 742 from certification. For example, if the certification stage at 714 fails to certify one or plural, or series of 2 or more, or a predefined fraction of a set of detected cardiac cycles, this may cause activation at block 740 or change the periodicity of block 740. In some examples, when noise or overdetection are identified in accordance with one or more thresholds, activation via block 740 may become more frequent or may be performed to confirm rate analysis from block 710.

In another example, block 740 may receive an input indicated at 744 from the X/Y filter. For example, when the X/Y filter at block 784 used by the tracking block 782 meets one or more thresholds, this may cause activation at block 740 or change the periodicity of block 740 to provide more frequent activation of block 720.

In another example, block 740 may observe characteristics of the rate as calculated by block 710 and/or 720. For example, if the rate(s) cross an absolute threshold 748, or if the rates change in excess of a threshold 750, this may cause activation at block 740 or change the periodicity of block 740 to provide more frequent activation of block 720. In an example, one or more absolute thresholds may be set at 100 to 200 bpm, such as at about 170 or 180 bpm, for example, or may be physician adjustable. In another example, a change or increase exceeding an absolute threshold (such as an increase in rate within a pre-specified period—for example, rate increases by 60 bpm in less than 20 seconds), or a percentage change (such as an increase or drop by more than 30%, which may again be time-constrained to 10, 20, or more seconds, up to a minute or more), may be sufficient.

In another example, block 740 may observe whether measured patient attributes match, as indicated at 752. For example, block 710 may be continuously active to generate a first rate, Rate 1, and block 740 may periodically activate block 720 at relatively long intervals (5 to 60 seconds, or more or less) to generate a second rate, Rate 2, and Rate 1 and Rate 2 may be compared as indicated at 754. An exact match may not be needed; generally block 754 may use a range such as plus/minus 10-40 bpm or 5-20%, for example. In another example, an activity sensor 756 (such as an accelerometer or a temperature sensor) may be used to provide an estimate of how active the patient is. The output of the activity sensor 756 can be used to provide an estimate of the expected cardiac rate for comparison to the rate from block 710—that is, a patient who is very active at a given time would not be expected to have a low rate, and an inactive patient would not be expected to have a high rate. If rates do not match at block 754, this may cause activation at block 740 or change the periodicity of block 740 to provide more frequent activation of block 720.

In another example, block 740 may be responsive to the activity sensor 756 directly. For example, when patient activity of increased level is detected at 756, this may cause activation at block 740 or change the periodicity of block 740 to provide more frequent activation of block 720. Increased activation would potentially be useful in particular for a patient who has had historical difficulty with device operation (inappropriate shock, for example) during exercise.

In another example, the input signal block 700 may be subject to filter selection 760. Filter selection 760 may operate, for example, as discussed in U.S. Provisional Patent Application 62/262,043, titled AUTOMATIC DETERMINATION AND SELECTION OF FILTERING IN A CARDIAC RHYTHM MANAGEMENT DEVICE, the disclosure of which is incorporated herein by reference. This dynamic filter selection 760 may occasionally change the filtering approach. When a change in filtering occurs, this may cause activation at block 740 or change the periodicity of block 740 to provide more frequent activation of block 720.

In another example, the input signal block 700 may be equipped to perform signal quality monitoring 762. Signal quality monitoring 762 may be performed, for example, as described in U.S. Provisional Patent Application 62/245,757, titled SIGNAL QUALITY MONITORING FOR MULTIPLE SENSE VECTORS IN CARDIAC DEVICES, the disclosure of which is incorporated herein by reference. Various metrics, such as the presence of noise, changes in amplitude, changes in signal-to-noise ratio, and others, are described in the copending application. When a drop or other change in signal quality, this may cause activation at block 740 or change the periodicity of block 740 to provide more frequent activation of block 720. In some examples, a drop in monitored signal amplitude may be a trigger. In some examples, the signal quality block 762 may further indicate that a sensing configuration change, such as a change in the sensing vector, is occurring or has taken place, and such a change may cause activation at block 740 or change the periodicity of block 740 to provide more frequent activation of block 720. Some examples for sense vector changes are shown in U.S. Provisional Patent Application 62/245,738, titled MULTI-VECTOR SENSING IN CARDIAC DEVICES WITH SIGNAL COMBINATIONS, U.S. Provisional Patent Application 62/245,762, titled MULTI-VECTOR SENSING IN CARDIAC DEVICES WITH DETECTION COMBINATIONS, and U.S. Provisional Patent Application 62/245,729, titled MULTI-VECTOR SENSING IN CARDIAC DEVICES USING A HYBRID APPROACH, the disclosures of which are incorporated herein by reference.

In another example, block 740 may receive an input from a posture sensor 770. A posture sensor may, for example, include an accelerometer, or may comprise circuitry or instruction sets for observing changes in transthoracic or other impedance that may be observed as a patient changes posture. When a change in patient posture is observed by posture sensor 770, this may cause activation at block 740 or change the periodicity of block 740 to provide more frequent activation of block 720.

In another example, block 740 may receive an input from a morphology calculator 772. For example, the morphology calculator 772 may compare detected cardiac cycles from block 712, or certified detected cardiac cycles from block 714, to a stored template that serves as a snapshot of the patient's cardiac electrical signal. If the morphology calculator 772 finds that the detected cycles or certified cycles fail to match the stored template repeatedly, this indicate a problem with the patient's cardiac rhythm such as a deleterious arrhythmia. Such a repeated mismatch observed at block 772 this may cause activation at block 740 or change the periodicity of block 740 to provide more frequent activation of block 720.

FIG. 15 shows an illustrative example in block form. Again the example includes a signal input block at 800, which provides signals to a block for a first calculation of rate at 810 and a second calculation of rate at 820. Block 810 may be continuously operated, while block 820 is activated at a lower rate in some examples—such as the various examples shown in FIG. 14, above. The first calculation of rate in block 810 may use cardiac cycle detection, as indicated at 812. The second calculation of rate at block 820 may use some other approach, such as analyzing signal blocks 822, obtaining rate information from a second device 824, or using a non-cardiac-electrical signal at 826, such as the examples described in FIG. 14, above.

The outputs of blocks 810 and, when active, 820, are provided to a decision block 830. The decision block 830 makes determinations of whether individual analytical outcomes suggest a treatable or monitor-able arrhythmia is ongoing. The outcomes from block 830 may be tracked as indicated at 832, using, for example, an X/Y filter 834. A declaration block 836 uses the decision block 830 and/or tracking 832 to decide whether the overall cardiac rhythm indicates an arrhythmia for monitoring or therapy.

The example of FIG. 15 is shown to more closely focus on a correction block 840, which may operate on the decision block 830 and tracking block 832, including the X/Y filter 834, when the rates calculated using the second calculation of rate 820 are provided. In some examples, data and/or analysis conclusions stored/used in blocks 830, 832, 834 may be confirmed by the second calculation of rate, in which case the correction block 840 may not perform any steps; the decision block 830 may modify stored data/analysis to indicate confirmation, if desired, when the outcomes of blocks 810 and 820 agree.

When there are differences between the outcomes from blocks 810 and 820, correction block 840 may use several approaches to applying corrections. In one example, the correction block 842 may drive re-evaluation 842 of some or all of the decisions 830 captured by the tracking block 832 and/or X/Y filter 834, for example as shown above in FIG. 12.

In another example, the correction block 840 may drive re-marking 844 or replacement of data stored by the X/Y filter 834. For example, the methods shown in FIGS. 9-13 illustrate how data may be re-marked 842 or even replaced.

In another example, the correction block 840 may operate as shown at 850. In this example, a set of outcomes 852 in the tracking block 832 or X/Y filter 834 are identified, and a period of time the outcomes 852 span is determined as shown at 854. In an alternative, the time block 854 may be preset, and the number of outcomes 852 occurring in the time block 854 are counted. An expected quantity of cardiac cycles is calculated at 856. The expected quantity of cardiac cycles would also represents the maximum number of analytical outcomes that would be expected to occur in the time block 854 using rate calculated by block 820. Block 858 then effects a change in the stored data to bring the number of outcomes 852 into alignment with the expected quantity.

For example, if the rate calculated by block 820 is 120 bpm (two cycles per second), and the time block 854 encompasses 4 seconds, then the expected quantity 856 would be eight (four seconds times two cycles per second). If there are fourteen outcomes 852, then the four of the outcomes would be cleared or set to a predefined result. For example, if the fourteen outcomes at 852 occurred in 4 seconds, this would suggest a detected rate of about 210 bpm, meaning each outcome 852 may be stored in the X/Y filter 834 as a treatable event. In one approach to block 850, the method would start with fourteen treatable events counted in the time block 854 stored in in the X/Y filter, and the change at 858 would reduce fourteen treatable events to eight treatable events in the X/Y filter, since only eight outcomes would be expected in that amount of time 854 given the 120 bpm rate. In another approach, that combines block 850 with block 842 and/or 844, not only would six outcomes be ignored from the X/Y filter 834, but the eight outcomes that remain would be changed from treatable to non-treatable, in light of the reduced cardiac rate of 120 bpm.

Another approach to correction 840 is shown at 860. Here, it is determined first whether the rate calculated at block 820 is in the VT or VF zone, as indicated at 862. Again, a corresponding block of time is then generated at 864, where the block of time may be a preset block of time in which the correction block 840 may determine how many analytical outcomes take place, or the block of time may be determined by seeing how long it takes for a selected quantity of analytical outcomes to occur, such as 8 to 24 outcomes. Using the block of time 864 and the rate from block 820, a predicted quantity of cardiac cycles for the block of time 864 is calculated at 866. If the number of detected cardiac cycles in the block of time 864 is less than the predicted number at 866, then an increase step or function is called at 868 to add to the number of markers stored in the tracking 832 or X/Y filter 834 that indicate an arrhythmia in the VT/VF zone. An example is shown above in FIG. 13.

Additional examples for combining together first and second cardiac rates are shown in U.S. Provisional Patent Application 62/262,048, titled METHODS AND DEVICES COMBINING MULTIPLE CARDIAC RATE MEASUREMENTS WITH INTERVAL CORRECTION AND ARRHYTHMIA DECISION BYPASS, the disclosure of which is incorporated herein by reference. These examples may be used in various combinations. For example:

An X/Y filter correction method shown above may be used in combination with a bypass block as illustrated in the 62/262,048 application. For example, the X/Y filter may be corrected in response to a single iteration of a second rate calculation and the X/Y filter may be bypassed after 2 or more persistent rate results from the second rate calculation.

An X/Y filter correction method shown above may be used in combination with beat buffer correction as illustrated in the 62/262,048 application. In this way, both current and previously generated data may be readily corrected throughout the arrhythmia analysis architecture.

In another example, the beat buffer correction methods shown in the 62/262,048 application may be used to correct data that is still in-process in the arrhythmia analysis architecture in response to a second rate calculation being different from a first rate calculation, and results from the beat buffer analysis may be bypassed after 2 or more persistent rate results from the second rate calculation.

Some implementations include operational circuitry for receiving a signal from implantable electrodes, processing the signal and analyzing the processed signal to make decisions such as whether to store data or deliver therapy. Operational circuitry may be housed in a canister or canisters. The operational circuitry may include a controller (such as a microcontroller or microprocessor, or simply an application specific integrated chip (ASIC) such as an analog, mixed signal, or digital ASIC). The operational circuitry may include suitable analog and/or digital circuits needed for signal processing, memory storage and generation of high-power electrical, low-power electrical and/or non-electrical outputs. The operational circuitry may include suitable battery technology for an implantable device (rechargeable or primary cell), with any of numerous examples well known in the art, and may use various capacitor technologies to assist in the short term build-up and/or storage of energy for defibrillation or other output purposes.

Implantable or wearable components may be manufactured with biocompatible materials suitable for implantation or tissue contact, such as those widely known, along with coatings for such materials, throughout the art. For example, implantable devices can be made using titanium, with a titanium nitride or iridium oxide (or other material) coating if desired, and implantable leads can be formed with a biocompatible material such as a polyether, polyester, polyamide, polyurethane, polycarbonate, silicon rubber and blends or copolymers thereof. Alternatively, other biocompatible materials such as silver, gold, titanium, or stainless steel such as MP35N stainless steel alloy, or other materials may be used.

In some examples, the system may include one or more sensors to detect signals in addition to the cardiac electrical signal that can be captured using selected combinations of implantable or wearable electrodes. Such additional sensors may include, for example, temperature sensors, accelerometers, microphones, optical sensors and chemical sensors, among others. The programmer 22 and implantable device 12 (FIG. 2) may communicate with one another using, for example and without limitation, inductive or RF telemetry, or any other suitable communication solution, including conducted communication. The present invention may be embodied in a system having any such characteristics.

In the following non-limiting examples, various means for performing certain functions are described with reference to block diagrams above. It should be understood, as noted above, that such blocks may represent dedicated circuitry/hardware, stored instruction sets for execution by a processor or controller, and/or combinations thereof.

A first non-limiting example takes the form of a cardiac rhythm management device comprising: signal means for receiving an cardiac electrical signal for analysis (such as input hardware 202 in FIG. 5, input signal 250 in FIG. 6, input signal 300 in FIG. 7, signal input 700 in FIG. 14, and/or signal input 800 in FIG. 15, discussed above); a first means for calculating cardiac rate, the first means configured to identify individual cardiac cycles in the cardiac electrical signal and determine a first cardiac rate (such as the certified beat detection event calculation 204 of FIG. 5, the sequence of blocks 252, 254, 256, and 258 in FIG. 6, the sequence of blocks 302, 304, 306 and 308 in FIG. 7, first calculation of rate 710 in FIG. 14 (with illustrative subparts 712, 714, 716), and/or first calculation of rate 810 that may use cardiac cycle detection 812, in FIG. 15); a second means for calculating cardiac rate, the second means configured to analyze a block of cardiac signal data and determine a second cardiac rate without identifying individual cardiac cycles (such as the autocorrelation heart rate estimation 210 in FIG. 5, block data analysis 272 in FIG. 6, block data analysis 322 in FIG. 7, second calculation of rate 720, using block analysis 722 in FIG. 14, and/or the second calculation of rate 820, using signal blocks 822, in FIG. 15); decision means for analyzing the individual cardiac cycles from the first means to decide which of the individual cardiac cycles indicates a treatable arrhythmia is ongoing (such as decision phase 220 in FIG. 5, decision phase 260 in FIG. 6, decision phase 310 in FIG. 7, decision block 780 in FIG. 14, and decision block 830 in FIG. 15); a counter means for counting a quantity of indications of treatable arrhythmia out of a set of analytical outcomes from the decision means (such as the X/Y filter 312 in FIG. 7, the tracking block 782 which may use an X/Y filter 784 in FIG. 14, and/or the tracking block 832 which may use an X/Y filter 834 as shown in FIG. 15); and correction means for correcting a value stored by the counter means in response to the second means for calculating cardiac rate finding a second cardiac rate which is different from the first cardiac rate (such as correction block 326 in FIG. 7, correction block 786 in FIG. 14, and/or correction block 840 in FIG. 15).

A second non-limiting example takes the form of a cardiac rhythm management device as in the first non-limiting example, wherein the correction means is configured to cause reevaluation of one or more individual cardiac cycles identified by the first means and analyzed by the decision means in light of the second cardiac rate (such as the reevaluation block 842 in FIG. 15).

A third non-limiting example takes the form of a cardiac rhythm management device as in either of the first or second non-limiting examples, wherein the counter means and decision means are configured such that each analytical outcome relates to one of the individual cardiac cycles, and correction means is configured to cause reevaluation, in light of the second cardiac rate, of each individual cardiac cycle related to an analytical outcome accounted for in the counter means (FIGS. 8-13 show illustrative operations of this sort; reevaluation block 842 is illustrated in FIG. 15).

A fourth non-limiting example takes the form of a cardiac rhythm management device as in either of the first or second non-limiting examples, wherein the counter means and decision means are configured such that each analytical outcome relates to one of the individual cardiac cycles, and wherein the correction means comprises: means to determine a time period to which a set of analytical outcomes accounted for in the counter means apply; means to determine an expected quantity of analytical outcomes in the determined time period, using the second cardiac rate; and means to change a value stored by the counter means if the expected quantity of analytical outcomes is different from the number of analytical outcomes in the set of analytical outcomes (FIGS. 8-13 show illustrative operations of this sort; correction block 840 in FIG. 15 take the form noted at 850 including counting outcomes 852, determining a period of time 854, calculating an expected quantity 856, and determining a change 858 for use by the correction block 840 to adjust tracking 832 and/or X/Y counter 834). A fifth non-limiting example takes the form of a cardiac rhythm management device as in the fourth non-limiting example, wherein the set of analytical outcomes comprises less than all analytical outcomes accounted for in the counter means (an example of this sort is shown in FIG. 10, where portions of the X/Y counter values are retained as indicated at 466 and 468).

A sixth non-limiting example takes the form of a cardiac rhythm management device as in the first non-limiting example wherein: the counter means and decision means are configured such that each analytical outcome relates to one of the individual cardiac cycles; and the correction means comprises: determining means to determine whether the second cardiac rate exceeds a therapy threshold for the device; change means to calculate a change value as follows: identify a period of time covered by a set of analytical outcomes accounted for in the counter means; determine how may analytical outcomes would be predicted to occur during the period of time using the second cardiac rate; and set the change value as the difference between the actual number of analytical outcomes and the predicted analytical outcomes; and the correction means is configured to change the counted quantity of indications of treatable arrhythmia stored by the counter means using the calculated change (FIG. 15 shows two examples of this type at 850 and again at 860, with the block at 860 showing an approach to the correction means 840 in which a VT/VF threshold is analyzed at 862, a period of time is assessed at 864 to yield a predicted quantity at 866 and the total number of indications of treatable arrhythmia may be increased as indicated at 868; such an example is also shown in FIG. 13).

A seventh non-limiting example takes the form of a cardiac rhythm management device as in the first non-limiting example wherein: the counter means and decision means are configured such that each analytical outcome relates to one of the individual cardiac cycles; and the correction means comprises: change means to calculate a change value as follows: identify a period of time covered by a set of analytical outcomes reflected in the counter means; identify how many of the set of analytical outcomes actually indicate arrhythmia; predict a number of analytical outcomes indicating arrhythmia that would occur during the period of time using the second cardiac rate; and set the change value as the difference between the actual number of analytical outcomes indicating arrhythmia and the predicted number of analytical outcomes indicating arrhythmia; and the correction means is configured to change the counted quantity of indications of treatable arrhythmia stored by the counter means using the calculated change value. As noted above, two approaches for such a correction means are shown at 850 and 860 in FIG. 15.

An eighth non-limiting example takes the form of a cardiac rhythm management device comprising: signal means for receiving an cardiac electrical signal for analysis (such as input hardware 202 in FIG. 5, input signal 250 in FIG. 6, input signal 300 in FIG. 7, signal input 700 in FIG. 14, and/or signal input 800 in FIG. 15, discussed above); a first means for calculating cardiac rate, the first means configured to continuously operate on the received cardiac electrical signal; (such as the certified beat detection event calculation 204 of FIG. 5, the sequence of blocks 252, 254, 256, and 258 in FIG. 6, the sequence of blocks 302, 304, 306 and 308 in FIG. 7, first calculation of rate 710 in FIG. 14 (with illustrative subparts 712, 714, 716), and/or first calculation of rate 810 that may use cardiac cycle detection 812, in FIG. 15); a second means for calculating cardiac rate, the second means configured to be activated in response to selected conditions (such as the autocorrelation heart rate estimation 210 in FIG. 5, block data analysis 272 in FIG. 6, block data analysis 322 in FIG. 7, and/or second calculation of rate 720, in FIG. 14 using block analysis 722, and/or the second calculation of rate 820, using signal blocks 822, in FIG. 15); and activation means for activating the second means for calculating cardiac rate to provide a calculated cardiac rate (such as the autocorrelation activation rules block 212 in FIG. 5, activation block 270 in FIG. 6, activation block 320 in FIG. 7, and/or activation block 740 in FIG. 14).

A ninth non-limiting example takes the form of a cardiac rhythm management device as in the eighth non-limiting example, wherein the first means for calculating cardiac rate comprises: detection means for detecting the occurrence of cardiac cycles by analysis of the cardiac signal; and certification means for certifying the cardiac cycles detected by the detection means are not caused by noise or overdetection of cardiac cycles (such elements of a first rate calculation means are shown in FIG. 6 at blocks 252, 254, in FIG. 7 at blocks 302, 304, and/or in FIG. 14 at blocks 712, 714); wherein the activation means is responsive to determination of the certification means that a least a threshold quantity, or fraction of a set, of detected cardiac cycles cannot be certified (such an example is shown in FIG. 14 where a determination from certification 742 can drive activation block 740).

A tenth non-limiting example takes the form of a cardiac rhythm management device as in either the eighth or ninth non-limiting examples, further comprising: decision means for deciding on an iterative basis whether an indication of cardiac arrhythmia is present (such as decision phase 220 in FIG. 5, decision phase 260 in FIG. 6, decision phase 310 in FIG. 7, decision block 780 in FIG. 14, and decision block 830 in FIG. 15); and tracking means for tracking outcomes from the decision means (such as the X/Y filter 312 in FIG. 7, the tracking block 782 which may use an X/Y filter 784 in FIG. 14, and/or the tracking block 832 which may use an X/Y filter 834 as shown in FIG. 15); wherein the activation means is responsive to the tracking means finding a predetermined quantity of outcomes indicate a cardiac arrhythmia is present (such as shown in FIG. 14 where block 744 can trigger activation block 740).

An eleventh non-limiting example takes the form of a cardiac rhythm management device as in the tenth non-limiting example, further comprising declaration means for declaring the presence of cardiac arrhythmia, using in part the tracking means, wherein the activation means is configured to activate the second means for calculating rate at a value, stored by the tracking means, that is less than a value required to declare the presence of cardiac arrhythmia (illustrations are shown in FIG. 8 where arrows 370 and 372 indicate triggers for the second rate means to activate at X/Y filter values below the therapy thresholds at 374 and/or 366).

A twelfth non-limiting example takes the form of a cardiac rhythm management device as in any of the eighth to eleventh non-limiting examples, further comprising correction means for correcting a value or values held by the tracking means if the second means for calculating cardiac rate finds a different rate than the first means for calculating cardiac rate (such as correction block 326 in FIG. 7, correction block 786 in FIG. 14, and/or correction block 840 in FIG. 15).

A thirteenth non-limiting example takes the form of a cardiac rhythm management device as in any of the eighth to twelfth non-limiting examples wherein the activation means is configured to activate the second means at least periodically as follows: if the first means for calculating a cardiac rate calculates a cardiac rate above a rate threshold, at a first period having a first duration; and if the first means for calculating a cardiac rate calculates a cardiac rate below the rate threshold, at a second period having a second duration longer than the first duration (FIG. 14 shows block 746 using rate 748 changing the periodicity of activation block 740).

A fourteenth non-limiting example takes the form of a cardiac rhythm management device as in any of the eighth to thirteenth non-limiting examples, further comprising: an activity sensor for calculating an activity level of a patient having the device; and matching means for matching an expected range of heart rate to the output of the activity sensor and comparing the expected range to the cardiac rate calculated by the first means for calculating cardiac rate; and wherein the activation means is configured to activate the second means for calculating cardiac rate in response to the matching means finding that the expected range does not match the calculated cardiac rate. (FIG. 14 illustrates the inclusion of a matching block 752 that can compare a rate to the output of an activity sensor 756, as described above, to trigger activation block 740).

A fifteenth non-limiting example takes the form of a cardiac rhythm management device as in any of the eighth to fourteenth non-limiting examples, further comprising a posture sensor for detecting a posture of a patient and determining whether and when the patient changes postures, wherein the activation means is configured to activate the second means for calculating cardiac rate in response to the posture sensor finding that the patient is or has recently changed postures (FIG. 14 illustrates inclusion of a posture sensor 770 to trigger activation block 740).

A sixteenth non-limiting example takes the form of a cardiac rhythm management device as in any of the eighth to fifteenth non-limiting examples further comprising morphology means for determining a morphological similarity of one cardiac cycle signal to a stored template of a normal cardiac cycle and generating a result showing either similarity or dissimilarity, wherein the activation means is configured to activate the second means for calculating cardiac rate in response to the morphology means finding dissimilarity for at least a threshold quantity of successive calculations or a threshold fraction of a set of successive calculations (FIG. 14 shows a morphology block 772 configured to trigger the activation block 740).

A seventeenth non-limiting example takes the form of a cardiac rhythm management device as in any of the eighth to sixteenth non-limiting examples, wherein the activation means is configured to activate the second means for calculating cardiac rate in response to a determination that the cardiac rate as calculated by the first means for calculating cardiac rate has changed by at least a threshold ratio or percentage in a predetermined period of time (FIG. 14 shows block 746 using a change of rate 750 to trigger the activation block 740).

An eighteenth non-limiting example takes the form of a cardiac rhythm management device as in any of the eighth to seventeenth non-limiting examples, wherein the signal means is configured to identify a low quality cardiac signal, wherein the activation means is configured to activate the second means for calculating cardiac rate in response to the low amplitude means finding a low quality cardiac signal (FIG. 14 shows the signal input block 700 providing a trigger based on signal quality 762 to the activation block 740).

A nineteenth non-limiting example takes the form of a cardiac rhythm management device as in any of the eighth to eighteenth non-limiting examples, wherein the signal means is configured to identify a low amplitude cardiac signal, wherein the activation means is configured to activate the second means for calculating cardiac rate in response to the low amplitude means finding a low amplitude cardiac signal. (FIG. 14 shows the signal input block 700 providing a trigger based on signal quality 762 to the activation block 740, and low amplitude signal is noted above as one of the measures of signal quality 762).

A twentieth non-limiting example takes the form of a cardiac rhythm management device as in any of the eighth to nineteenth non-limiting examples, wherein the signal means includes a filter selector means for selecting between first and second filter settings, and the activation means is configured to activate the second means for calculating a cardiac rate at least periodically as follows: if the first filter setting is selected by the filter selector means, at a first period having a first duration; and if the second filter setting is selected by the filter selector means, at a second period having a second duration longer than the first duration (FIG. 14 shows a filter selection block 760 for operating on the signal input block 700 as well as triggering the activation block 740).

A twenty-first non-limiting example takes the form of a cardiac rhythm management device as in any of the eighth to twentieth non-limiting examples wherein: the first means for calculating a cardiac rate operates by detecting individual cardiac cycles (such as the certified beat detection event calculation 204 of FIG. 5, the sequence of blocks 252, 254, 256, and 258 in FIG. 6, the sequence of blocks 302, 304, 306 and 308 in FIG. 7, first calculation of rate 710 in FIG. 14 (with illustrative subparts 712, 714, 716), and/or first calculation of rate 810 that may use cardiac cycle detection 812, in FIG. 15); and the second means for calculating a cardiac rate operates by comparing a segment of the cardiac electrical signal to one or more segments of the cardiac electrical signal to identify a periodicity of the cardiac electrical signal and generating a rate from the periodicity (such as the method shown in FIG. 4 and referenced as autocorrelaton at block 726 in FIG. 14, as well as several other places above).

A twenty-second non-limiting example takes the form of an implantable defibrillator system comprising a device as in any of the first to twenty-first non-limiting examples (an implantable defibrillator is shown in FIG. 1, above). A twenty-third non-limiting example takes the form of a wearable defibrillator system comprising a device as in any of the first to twenty-first non-limiting examples (several examples of wearable systems are discussed above).

A twenty-fourth non-limiting example takes the form of a cardiac rhythm management device comprising a canister housing operational circuitry and having a port adapted for use with an implantable lead having a plurality of electrodes such that multiple sensing electrodes for sensing a cardiac electrical signal are available, with operational circuitry coupled to the port and configured to perform cardiac signal analysis comprising: receiving a cardiac electrical signal for analysis; calculating a first cardiac rate by identifying individual cardiac cycles in the cardiac electrical signal; calculating a second cardiac rate without identifying cardiac cycles by analysis of a block of cardiac signal data; analyzing the individual cardiac cycles to decide which of the individual cardiac cycles indicates a treatable arrhythmia is ongoing to yield a set of analytical outcomes; counting a quantity of indications of treatable arrhythmia out in the set of analytical outcomes and storing the quantity; and determining whether the second cardiac rate is different from the first cardiac rate and, if so, correcting the stored quantity to remove one or more overdetections.

A twenty-fifth non-limiting example takes the form of a cardiac rhythm management device as in the twenty-fourth non-limiting example, wherein the operational circuitry is configured to perform the step of correcting the stored quantity by reevaluating one or more individual cardiac cycles in light of the second cardiac rate.

A twenty-sixth non-limiting example takes the form of a cardiac rhythm management device as in the twenty-fourth non-limiting example, wherein the operational circuitry is configured such that each of the analytical outcomes relates to one of the individual cardiac cycles, and the step of correcting the stored quantity is performed by reevaluating each individual cardiac cycle related to an analytical outcome in the set of analytical outcomes.

A twenty-seventh non-limiting example takes the form of a cardiac rhythm management device as in the twenty-fourth non-limiting example, wherein: the operational circuitry is configured such that each of the analytical outcome relates to one of the individual cardiac cycles; and the operational circuitry is configured to determine whether the second cardiac rate is in a treatable arrhythmia zone and, if so, the step of correcting the stored quantity is performed by: determining a time period to which the set of analytical outcomes applies; calculating an expected quantity of analytical outcomes in the determined time period using the second cardiac rate; and if the stored quantity does not match the expected quantity, changing the stored quantity to match the expected quantity.

A twenty-eighth non-limiting example takes the form of a cardiac rhythm management device as in the twenty-fourth non-limiting example, wherein: the operational circuitry is configured such that each of the analytical outcome relates to one of the individual cardiac cycles; the second cardiac rate is calculated iteratively at an interval; and the operational circuitry is configured to determine whether the second cardiac rate is below a treatable arrhythmia zone and, if so, the step of correcting the stored quantity is performed by reducing the stored quantity by the number of indications of treatable arrhythmia that were generated during the interval.

A twenty-ninth non-limiting example takes the form of a cardiac rhythm management device comprising a canister housing operational circuitry and having a port adapted for use with an implantable lead having a plurality of electrodes such that multiple sensing electrodes for sensing a cardiac electrical signal are available, with operational circuitry coupled to the port and configured to perform cardiac signal analysis comprising: receiving a cardiac electrical signal for analysis; calculating a first cardiac rate by identifying individual cardiac cycles in the cardiac electrical signal; and calculating a second cardiac rate without identifying cardiac cycles by analysis of a block of cardiac signal data, wherein the step of calculating the second cardiac rate is performed in response to activation by the operational circuitry in response to one or more predetermined conditions.

A thirtieth non-limiting example takes the form of a cardiac rhythm management device as in the twenty-ninth non-limiting example, wherein the operational circuitry is configured such that the step of calculating the first cardiac rate is performed by: detecting the occurrence of cardiac cycles by analysis of the cardiac signal; analyzing the detected cardiac cycles to identify noise and overdetection; and certifying cardiac cycles not caused by noise or overdetection of cardiac cycles for generating a set of cycle intervals from which the first cardiac rate is calculated; wherein the operational circuitry is further configured to determine whether the certification step finds that a least a threshold quantity, or fraction of a set, of detected cardiac cycles cannot be certified and, if so, to activate the step of calculating the second cardiac rate.

A thirty-first non-limiting example takes the form of a cardiac rhythm management device as in the twenty-ninth non-limiting example, wherein the operational circuitry is configured to: decide on an iterative basis whether an indication of cardiac arrhythmia is present using at least the first cardiac rate to yield a set of analytical outcomes; and tracking the analytical outcomes in an X/Y counter; wherein the operational circuitry is configured to activate the second cardiac rate calculation in response to the X/Y counter reaching a first predetermined threshold.

A thirty-second non-limiting example takes the form of a cardiac rhythm management device as in the thirty-first non-limiting example, wherein the operational circuitry is configured to declare a treatable arrhythmia is occurring in response to predetermined conditions including at least that the X/Y counter reach a second predetermined threshold, wherein the first predetermined threshold is lower than the second predetermined threshold.

A thirty-third non-limiting example takes the form of a cardiac rhythm management device as in the thirty-first non-limiting example, wherein the operational circuitry is configured to determine whether the first cardiac rate is the same as the second cardiac rate and, if not, to correct a value stored in the X/Y counter if predetermined criteria are met.

A thirty-fourth non-limiting example takes the form of a cardiac rhythm management device as in the twenty-ninth non-limiting example, wherein the operational circuitry is configured to activate the second cardiac rate calculation periodically as follows: if the first cardiac rate is above a rate threshold, at a first period having a first duration; and if the first cardiac rate is below the rate threshold, at a second period having a second duration longer than the first duration.

A thirty-fifth non-limiting example takes the form of a cardiac rhythm management device as in the twenty-ninth non-limiting example, further comprising an activity sensor for calculating an activity level of a patient having the device; wherein the operational circuitry is configured to activate the second cardiac rate calculation by: obtaining an activity level from the activity sensor; determining whether the first cardiac rate matches the activity level; and if the activity level and the first cardiac rate do not match, activating the second cardiac rate calculation.

A thirty-sixth non-limiting example takes the form of a cardiac rhythm management device as in the twenty-ninth non-limiting example, further comprising a posture sensor for detecting a posture of a patient and determining whether and when the patient changes postures, wherein the operational circuitry is configured to activate the second cardiac rate calculation in response to the posture sensor finding that the patient is or has recently changed postures.

A thirty-seventh non-limiting example takes the form of a cardiac rhythm management device as in the twenty-ninth non-limiting example, wherein the operational circuitry is further configured to determine a morphological similarity of one cardiac cycle signal to a stored template of a normal cardiac cycle and generate a result showing either similarity or dissimilarity; further wherein the operational circuitry is configured to activate the second cardiac rate calculation in response to finding dissimilarity for at least a threshold quantity of successive calculations or a threshold fraction of a set of successive calculations of morphological similarity.

A thirty-eighth non-limiting example takes the form of a cardiac rhythm management device as in the twenty-ninth non-limiting example, wherein the operational circuitry is configured to activate the second cardiac rate calculation in response to the first cardiac rate changing by at least a threshold ratio or percentage in a predetermined period of time.

A thirty-ninth non-limiting example takes the form of a cardiac rhythm management device as in the twenty-ninth non-limiting example, wherein the operational circuitry is configured to identify a low quality cardiac signal and activate the second cardiac rate calculation in response to identification of a low quality cardiac signal.

A fortieth non-limiting example takes the form of a cardiac rhythm management device as in the twenty-ninth non-limiting example, wherein the operational circuitry is configured to identify a low amplitude cardiac signal and activate the second cardiac rate calculation in response to identification of a low amplitude cardiac signal.

A forty-first non-limiting example takes the form of a cardiac rhythm management device as in the twenty-ninth non-limiting example, wherein the operational circuitry comprises a selectable filter configuration having at least first and second selectable configurations, and the operational circuitry is configured to activate the second cardiac rate calculation in response to a change of the selectable filter configuration.

A forty-second non-limiting example takes the form of a cardiac rhythm management device as in the twenty-ninth non-limiting example, wherein the operational circuitry comprises a selectable filter configuration having at least first and second selectable filter configurations available for use, and the operational circuitry is configured to periodically activate the second cardiac rate measurement as follows: at a first period having a first duration if the first selectable filter configuration is in use; or at a second period having a second duration longer than the first duration if the second selectable filter configuration is in use.

A forty-third non-limiting example takes the form of a cardiac rhythm management device as in the twenty-ninth non-limiting example, wherein the operational circuitry is configured such that: the first cardiac rate calculation operates by detecting individual cardiac cycles; and the second cardiac rate calculation operates by comparing a segment of the cardiac electrical signal to one or more segments of the cardiac electrical signal to identify a periodicity of the overall signal, and generating a rate from the periodicity.

A forty-fourth non-limiting example takes the form of an implantable defibrillator system comprising a device as in any of the twenty-fourth to forty-third non-limiting examples. A forty-fifth non-limiting example takes the form of a wearable defibrillator system comprising a device as in any of the twenty-fourth to forty-third non-limiting examples.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls. In this document, the terms "a" or "an" are used, as is common in patent documents, to include one or more than one, independent of any other instances or usages of "at least one" or "one or more." Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic or optical disks, magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description.

The Abstract is provided to comply with 37 C.F.R. § 1.72(b), to allow the reader to quickly ascertain the nature of the technical disclosure. It is submitted with the understanding that it will not be used to interpret or limit the scope or meaning of the claims.

Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A cardiac rhythm management device comprising a canister housing operational circuitry and having a port adapted for use with an implantable lead having a plurality of electrodes such that multiple sensing electrodes for sensing cardiac electrical signals are available, with operational circuitry coupled to the port and configured to perform cardiac signal analysis comprising:
    calculating a first cardiac rate by identifying individual cardiac cycles in a first cardiac electrical signal;
    calculating a second cardiac rate by analysis of a second cardiac electrical signal, without identifying cardiac cycles, wherein the step of calculating the second cardiac rate is performed in response to activation by the operational circuitry in response to one or more predetermined conditions;
    comparing at least one of the first cardiac rate and the second cardiac rate to a rate threshold;
    determining whether a cardiac arrhythmia is present based on the comparison between at least one of the first cardiac rate and the second cardiac rate to the rate threshold; and
    in response to determining the cardiac arrhythmia is present, performing at least one of:
        preparation for delivering therapy;
        delivering therapy; and
        storing cardiac electrical signal data.

2. The cardiac rhythm management device of claim 1 wherein the operational circuitry is configured such that the step of calculating the first cardiac rate is performed by:
    detecting the occurrence of cardiac cycles by analysis of the cardiac signal;
    analyzing the detected cardiac cycles to identify noise and overdetection; and
    certifying cardiac cycles not caused by noise or overdetection of cardiac cycles for generating a set of cycle intervals from which the first cardiac rate is calculated;
    wherein the operational circuitry is further configured to determine whether the certification step finds that at least a threshold quantity, or fraction of a set, of detected cardiac cycles cannot be certified and, if so, to activate the step of calculating the second cardiac rate.

3. The cardiac rhythm management device of claim 1 wherein the operational circuitry is configured to:
    decide on an iterative basis whether the indication of cardiac arrhythmia is present using at least the first cardiac rate to yield a set of analytical outcomes; and
    track the analytical outcomes in an X/Y counter;
    wherein the operational circuitry is configured to activate the second cardiac rate calculation in response to the X/Y counter reaching a first predetermined threshold.

4. The cardiac rhythm management device of claim 3 wherein the operational circuitry is configured to declare a treatable arrhythmia is occurring in response to predetermined conditions including at least that the X/Y counter reach a second predetermined threshold, wherein the first predetermined threshold is lower than the second predetermined threshold.

5. The cardiac rhythm management device of claim 3 wherein the operational circuitry is configured to determine whether the first cardiac rate is the same as the second cardiac rate and, if not, to correct a value stored in the X/Y counter if predetermined criteria are met.

6. The cardiac rhythm management device of claim 1 wherein the operational circuitry is configured to activate the second cardiac rate calculation periodically as follows:
    if the first cardiac rate is above the rate threshold, at a first period having a first duration; and
    if the first cardiac rate is below the rate threshold, at a second period having a second duration longer than the first duration.

7. The cardiac rhythm management device of claim 1 further comprising an activity sensor for calculating an activity level of a patient having the device;
wherein the operational circuitry is configured to activate the second cardiac rate calculation by:
obtaining an activity level from the activity sensor;
determining whether the first cardiac rate matches the activity level; and
if the activity level and the first cardiac rate do not match, activating the second cardiac rate calculation.

8. The cardiac rhythm management device of claim 1 further comprising a posture sensor for detecting a posture of a patient and determining whether and when the patient changes postures, wherein the operational circuitry is configured to activate the second cardiac rate calculation in response to the posture sensor finding that the patient is or has recently changed postures.

9. The cardiac rhythm management device as in claim 1 wherein the operational circuitry is further configured to determine a morphological similarity of one cardiac cycle signal to a stored template of a normal cardiac cycle and generate a result showing either similarity or dissimilarity; further wherein the operational circuitry is configured to activate the second cardiac rate calculation in response to finding dissimilarity for at least a threshold quantity of successive calculations or a threshold fraction of a set of successive calculations of morphological similarity.

10. The cardiac rhythm management device as in claim 1 wherein the operational circuitry is configured to activate the second cardiac rate calculation in response to the first cardiac rate changing by at least a threshold ratio or percentage in a predetermined period of time.

11. The cardiac rhythm management device as in claim 1 wherein the operational circuitry is configured such that:
the first cardiac rate calculation operates by detecting individual cardiac cycles; and
the second cardiac rate calculation operates by comparing a segment of the second cardiac electrical signal to one or more segments of the second cardiac electrical signal to identify a periodicity of the overall signal, and generating a rate from the periodicity.

12. The cardiac rhythm management device of claim 1 wherein the first cardiac electrical signal is the same cardiac electrical signal as the second cardiac electrical signal.

13. The cardiac rhythm management device of claim 1 wherein the first cardiac electrical signal is a different cardiac electrical signal than the second cardiac electrical signal.

14. A method of cardiac signal analysis performed by a cardiac rhythm management device having a canister housing operational circuitry and having a port adapted for use with an implantable lead having a plurality of electrodes such that multiple sensing electrodes for sensing cardiac electrical signals are available, with the operational circuitry coupled to the port, the method comprising:
calculating a first cardiac rate by identifying individual cardiac cycles in a first cardiac electrical signal;
calculating a second cardiac rate by analysis of a second cardiac electrical signal, without identifying cardiac cycles, wherein the step of calculating the second cardiac rate is performed in response to activation by the operational circuitry in response to one or more predetermined conditions
comparing at least one of the first cardiac rate and the second cardiac rate to a rate threshold;
determining whether a cardiac arrhythmia is present based on the comparison between the at least one of the first cardiac rate and the second cardiac rate to the rate threshold; and
in response to determining the cardiac arrhythmia is present, performing at least one of:
preparation for delivering therapy;
delivering therapy; and
storing cardiac electrical signal data.

15. The method of claim 14 wherein the step of calculating the first cardiac rate is performed by:
detecting the occurrence of cardiac cycles by analysis of the cardiac signal;
analyzing the detected cardiac cycles to identify noise and overdetection; and
certifying cardiac cycles not caused by noise or overdetection of cardiac cycles for generating a set of cycle intervals from which the first cardiac rate is calculated;
wherein the method comprises activating the step of calculating the second cardiac rate in response to finding that at least a threshold quantity, or fraction of a set, of detected cardiac cycles cannot be certified in the certifying step.

16. The method of claim 14 further comprising:
deciding on an iterative basis whether the indication of cardiac arrhythmia is present using at least the first cardiac rate to yield a set of analytical outcomes;
tracking the analytical outcomes in an X/Y counter; and
activating the second cardiac rate calculation in response to the X/Y counter reaching a first predetermined threshold.

17. The method of claim 14 further comprising activating the second cardiac rate calculation periodically as follows:
if the first cardiac rate is above the rate threshold, at a first period having a first duration; and
if the first cardiac rate is below the rate threshold, at a second period having a second duration longer than the first duration.

18. The method of claim 14 wherein the cardiac rhythm management device includes an activity sensor for calculating an activity level of a patient having the device, and the method further comprises:
obtaining an activity level from the activity sensor;
determining whether the first cardiac rate matches the activity level; and
if the activity level and the first cardiac rate do not match, activating the second cardiac rate calculation.

19. The method of claim 14 wherein the first cardiac electrical signal is the same cardiac electrical signal as the second cardiac electrical signal.

20. The method of claim 14 wherein the first cardiac electrical signal is a different cardiac electrical signal than the second cardiac electrical signal.

* * * * *